(12) United States Patent
Bonnet et al.

(10) Patent No.: US 11,986,374 B2
(45) Date of Patent: May 21, 2024

(54) METHOD AND SYSTEM FOR MEASURING IN-EAR EFFECTIVE SOUND EXPOSURE UNDER AN EARPLUG OR WITHOUT AN EARPLUG AND FOR DETERMINING A WEARER INDUCED DISTURBANCE

(71) Applicants: Ecole de technologie superieure, Montreal (CA); IRSST—INSTITUT DE RECHERCHE EN SANTE ET EN SECURITE DU TRAVAIL DU QUEBEC, Montreal (CA)

(72) Inventors: Fabien Bonnet, Montreal (CA); Jeremie Voix, Montreal (CA); Hugues Nelisse, Montreal (CA); Marcos Nogarolli, Montreal (CA)

(73) Assignee: ECOLE DE TECHNOLOGIE SUPERIEURE, Montreal (CA)

( * ) Notice: Subject to any disclaimer, the term of this patent is extended or adjusted under 35 U.S.C. 154(b) by 722 days.

(21) Appl. No.: 17/053,853

(22) PCT Filed: May 9, 2019

(86) PCT No.: PCT/CA2019/050625
§ 371 (c)(1),
(2) Date: Nov. 9, 2020

(87) PCT Pub. No.: WO2019/213773
PCT Pub. Date: Nov. 14, 2019

(65) Prior Publication Data
US 2021/0236339 A1  Aug. 5, 2021

Related U.S. Application Data

(60) Provisional application No. 62/669,177, filed on May 9, 2018.

(51) Int. Cl.
*A61F 11/08* (2006.01)
*A61B 5/00* (2006.01)
(Continued)

(52) U.S. Cl.
CPC ............... *A61F 11/08* (2013.01); *A61B 5/12* (2013.01); *A61B 5/6817* (2013.01);
(Continued)

(58) Field of Classification Search
CPC .......... A61F 11/08; A61F 11/145; A61B 5/12; A61B 5/6817; A61B 5/7278;
(Continued)

(56) References Cited

U.S. PATENT DOCUMENTS 4,809,708 A * 3/1989 Geisler ................. A61B 5/121
600/552
4,827,525 A * 5/1989 Hotvet ................. H04R 25/604
381/60

(Continued)

OTHER PUBLICATIONS

Supplementary European Search Report dated Jan. 4, 2022 in the corresponding European patent application No. 19800489.7.
(Continued)

*Primary Examiner* — Oyesola C Ojo
(74) *Attorney, Agent, or Firm* — Brouillette Legal Inc.; Robert Brouillette

(57) ABSTRACT

Personalised calibration methods and devices adapted to identify acoustical corrections to be applied for in-ear dosimetry. The acoustical corrections allow to convert a measured acoustic pressure within the ear-canal of a user to an equivalent acoustic pressure at the ear-drum and/or in free-field. The methods and devices also allow to distinguish noises originating from the user from noises of the environment in the ear occluded by an earplug. Such a distinction is done using two microphones to simultaneously measure
(Continued)

the acoustic pressure within the ear-canal and outside the ear-canal. The device may be used to determine a cumulative sound pressure level dosage for which a user being exposed to surrounding sounds over a predetermined period of time.

18 Claims, 16 Drawing Sheets

(51) Int. Cl.
    *A61B 5/12*     (2006.01)
    *H04R 29/00*     (2006.01)

(52) U.S. Cl.
    CPC .......... *A61B 5/7278* (2013.01); *H04R 29/00* (2013.01); *A61B 2503/20* (2013.01); *A61B 2560/0223* (2013.01)

(58) Field of Classification Search
    CPC ........ A61B 2503/20; A61B 2560/0223; A61B 5/126; A61B 5/4884; H04R 29/00; H04R 2460/15; H04R 1/1016; H04R 1/1083; G01H 3/12
    See application file for complete search history.

(56) References Cited

U.S. PATENT DOCUMENTS

| | | | |
|---|---|---|---|
| 5,044,373 A * | 9/1991 | Northeved | H04R 25/70 600/559 |
| 8,462,956 B2 | 6/2013 | Goldstein et al. | |
| 2002/0076057 A1 * | 6/2002 | Voix | H04R 25/30 381/328 |
| 2008/0144842 A1 * | 6/2008 | Goldstein | H04R 1/1083 381/56 |
| 2012/0177210 A1 * | 7/2012 | Goldstein | G01H 3/14 381/58 |
| 2012/0300951 A1 | 11/2012 | Voix et al. | |
| 2017/0312135 A1 * | 11/2017 | Parkins | H04R 1/1083 |

OTHER PUBLICATIONS

International Search Report dated Aug. 8, 2019 in the corresponding International patent application No. PCT/CA2019/050625.

* cited by examiner

METHOD AND SYSTEM FOR MEASURING IN-EAR EFFECTIVE SOUND EXPOSURE UNDER AN EARPLUG OR WITHOUT AN EARPLUG AND FOR DETERMINING A WEARER INDUCED DISTURBANCE

CROSS-REFERENCE TO RELATED APPLICATIONS

The present patent application claims priority of U.S. provisional patent application No. 62/669,177 filed on May 9, 2018, the content of which is incorporated herein.

TECHNICAL FIELD

The present solution relates to the field of noise exposure measurement. More particularly, the present solution relates to the field of in-ear effective sound exposure.

BACKGROUND

Every day, hundreds of millions of workers worldwide are exposed to noise levels that are likely to affect their hearing. Noise at work remains a major concern, not only in developing nations, but also in many developed countries. In 2000, 7% of European workers reported that their work activities had affected their health and led to hearing disorders. And yet, noise-induced hearing loss (NIHL) is in practice avoidable, provided that excessive noise exposure of the affected workers is detected before it is too late. Unfortunately, all too often, the safety measures that could prevent NIHL are not applied because the workers at risk are not actually aware that they are putting their hearing at risk. Such measures may include noise control measures, the use of appropriate hearing protection devices (HPDs), or administrative controls like the introduction of shorter working hours. To ensure the timely implementation of such measures, it is essential that the noise exposure levels of any given individual be precisely established in the workplace.

Personal noise exposure measurements aim to assess the noise exposure of a person, usually a worker, to ensure compliance with the occupational exposure limits of a given legislation. Such assessment is typically done through the determination of two variables: the ambient (unprotected) noise levels received by the individual, and the attenuation provided by the HPD (if HPDs are worn). The ambient noise levels can be estimated using standard sound level meters or, for more precision, by using personal body-mounted dosimeters. Personal noise dosimeters are particularly useful in situations in which the acoustical environment varies significantly over time, as these devices can track sound exposure near the ears of the individual (they are usually worn on the shoulder). Nevertheless, these present issues related to microphone placement effects and the influence of the wearer's voice on noise measurements, and cannot account for the attenuation provided by potential HPDs. Moreover, despite the progress achieved to estimate the field performance of HPDs, current fit-testing methods still suffer from a number of uncertainties that make it difficult to establish the effective attenuation of a particular HPD on a given individual. Finally, personal noise dosimeters only provide information about the ambient noise levels, hence failing to account for wearer placement effects and inter-individual differences in the wearers' ear geometries. Different people subjected to the same ambient noise level may indeed receive significantly different sound pressure levels (SPLs) at the eardrum, and the in-ear SPLs received by a given person may also vary as a function of the latter's head and body orientation. And while the damage risk criteria of existing noise standards refer to free-field measurements, it is commonly believed that the risk of hearing loss is more directly related to the levels received at the tympanic membrane or eardrum.

In light of the aforementioned issues, promising systems providing continuous monitoring of an individual's noise exposure directly inside the ear have begun to emerge. Not only are these systems able to account for HPD attenuation, but they are also sensitive to the effects of the wearer's placement and to the unique shape of each individual's ears.

However, current in-ear noise dosimeters (IENDs) do not allow direct collection of eardrum data, as their featuring in-ear microphone is typically maintained at a certain distance from the membrane for comfort and safety reasons. Hence, a correction is needed to convert the measured SPLs to the eardrum. Although an average correction can be used, such as that measured on a mannequin, individual correction factors should provide better results by considering the very distinct geometry of every ear canal. Moreover, personal noise exposure measurements aim to assess the amount of noise exposure for a person, usually a worker, to ensure this amount complies with the exposure limits of a given legislation. One way of monitoring the level of exposure is a personal body-worn dosimeter, which provides the convenience of continuous monitoring at the location of the individual. Personal noise dosimeters are particularly useful when individuals are required to move frequently during their work shift or when the acoustic environment of the workplace is hardly predictable, since such variables cannot be taken into account with standard sound level meter measurements. These are usually attached to the wearer's shoulder to measure the noise levels close to the ears. Though adequate, this location does not always counter the effect of microphone placement, particularly for directional sound fields. Also, the measured sound pressure levels (SPLs) may not represent the ambient noise correctly if influenced by the wearer's voice. And furthermore, the accuracy of personal noise dosimeters is compromised when hearing protection devices (HPDs) are worn. Indeed, the attenuation provided by the HPD, which should be subtracted from the ambient noise levels, can show large variations and uncertainties. Despite the progress achieved in the estimation of the field performance of HPDs, current fit-testing methods are beset by major uncertainties such as Measurement Uncertainty, Spectrum Uncertainty and Fit Variability, and also fail to account for HPD removal. Such uncertainties both in the ambient noise levels and in the HPD's effective attenuation make it difficult to accurately determine the actual noise exposure received by a given worker wearing HPDs over a period of time.

Several have developed systems that continuously monitor an individual's noise exposure under the HPD. But to accurately determine if an individual is properly protected against noise, the influence of self-induced sounds on in-ear noise dosimeter measurements needs to be considered, since the SPLs measured below HPDs may be significantly affected by noise emitted by the wearer. This is particularly true when earplugs are worn, as the so-called occlusion effect (OE) is known to amplify most sounds originating from the wearer, especially at low frequencies. Such sounds, which will be further referred to as wearer-induced disturbances (WIDs), may result from shouting, speaking, singing, coughing or sneezing, but softer sounds associated with chewing, walking, scratching, sniffing, or swallowing may also need to be considered in low ambient noise environments. Indeed, research has previously shown that the risk of hearing loss inherent to self-generated noise can be less than that of external noise due to inhibition mechanisms occurring both in the middle ear and at the neuronal level. Moreover, the OE tends to amplify non-physiological noise emanating from the interaction between the measuring instrument and the wearer, such as rustling and thumping noises (often referred to as microphonics) one hears when tapping the earpiece's cord or when the cord brushes against something.

Therefore, there is a need to measure the average noise exposure excluding the noise produced by the individual, especially when earplugs are worn. Moreover, there is a need to convert the measured SPLs within the ear to equivalent SPLs at the tympanic membrane (eardrum) and/or to equivalent free-field SPLs.

SUMMARY

The aforesaid and other objectives of the present invention are realized by generally providing a method and an earpiece for estimating an effective in-ear sound pressure level of an ear canal for an individual.

In one aspect of the invention, a method for estimating an effective in-ear sound pressure level of an ear canal for an individual is provided. The method comprises capturing a baseline outer-ear sound pressure level outside the ear canal, capturing a baseline in-ear sound pressure level at an intermediate position of the ear canal, determining a correction factor according to the captured baseline outer-ear sound pressure level and the captured baseline in-ear sound pressure level, while the ear canal is unoccluded, capturing a first sound pressure level at the intermediate position of the ear canal and estimating the effective in-ear sound pressure level according to the determined correction factor and the captured first sound pressure level.

The first sound pressure level may be captured behind a hearing protection device. Estimating the effective in-ear sound pressure level may be converting the measured first sound pressure level in an equivalent free field sound pressure level. The correction factor may be calculated by subtracting the captured baseline in-ear sound pressure level from the captured baseline outer-ear sound pressure level.

Estimating the effective in-ear sound pressure level may be converting the captured first sound pressure level in an equivalent tympanic sound pressure level. Determining the correction factor may further comprise identifying a predetermined filter and a standing-wave minimum frequency according a difference between the captured baseline in-ear sound pressure level and the captured baseline outer-ear sound pressure level.

The method may further comprise capturing a second sound pressure level from outside the ear canal simultaneously with the capturing of the first sound pressure level, wherein the effective in-ear sound pressure level is further estimated according to the captured second sound pressure level. The estimating of the effective in-ear sound pressure level may further comprise calculating an average ratio between two transfer functions associated to the captured first and the second sound pressure levels. The average ratio between two transfer functions may be determined for frequencies between a predetermined minimum frequency and a predetermined maximum frequency. The average ratio between two transfer functions may be associated to the captured first and second sound pressure levels is defined as:

$$\Delta_i = -10\log_{10}\left(\frac{\sum_{f_p=f_{min}}^{f_p=f_{max}} \gamma_i^2(f_p)}{N}\right) \quad (2)$$

The method may further comprise detecting wearer induced disturbance, wherein the effective in-ear noise level is further estimated according to the detected wearer induced disturbance. The effective in-ear noise level may further be estimated according to a noise level of the detected wearer induced disturbance, for frequencies between a predetermined minimum frequency and a predetermined maximum frequency. The noise level of the detected wearer induced disturbance may be determined by comparing the captured first sound pressure level to a noise level threshold value. The effective in-ear sound pressure level may be estimated according to the captured second sound pressure level when a wearer induced disturbance is detected and when the noise level of the captured first sound pressure level is lower than the noise level threshold.

The wearer induced disturbance may be detected according to a coherence function between the captured first sound pressure level and the captured second sound pressure level. The wearer induced disturbance may further be detected according to an average of the coherence function over a predetermined frequency range. Yet, the wearer induced disturbance may be detected when the average of the coherence function is greater than a predetermined threshold value. The effective in-ear sound pressure level may be estimated by ignoring the detected wearer induced disturbance. The effective in-ear sound pressure level may further be estimated according to the captured second sound pressure level and an estimated noise reduction. The estimated noise reduction may be determined according to the captured first sound pressure level and the captured second sound pressure level performed when the average of the coherence function was lower than the threshold value.

The effective in-ear sound pressure level may be estimated according to the captured first sound pressure level performed when the average of the coherence function was lower than the threshold value. The wearer induced disturbance may have a noise level that is lower than a predetermined threshold noise level or a noise level that is higher than a predetermined threshold noise level.

In another aspect of the invention, a method for detecting a wearer induced disturbance from an ear canal of an individual is provided. The method comprises capturing a first sound pressure level at an intermediate position of an ear canal, capturing a second sound pressure level outside the ear canal simultaneously as the first sound pressure level and detecting the wearer induced disturbance according to a coherence function between the captured first sound pressure level and the captured second sound pressure level.

The wearer induced disturbance may be detected according to an average of the coherence function over a predetermined frequency range or may be detected when the average of the coherence function is greater than a threshold value. The average of the coherence function over the predetermined frequency range may be determined as:

$$\Delta_i = -10\log_{10}\left(\frac{\sum_{f_p=f_{min}}^{f_p=f_{max}} \gamma_i^2(f_p)}{N}\right) \quad (2)$$

The predetermined frequency range may be between 500 Hz and 2000 Hz, between 500 Hz and 1500 Hz or between 500 Hz and 1000 Hz.

The method may further comprises further characterizing a type of the detected wearer induced disturbance according to the captured first sound pressure level. The detected wearer induced disturbance may be characterized as a low-level noise when the captured first sound pressure level is below a predetermined noise threshold level and as a high-level noise if the captured first sound pressure level is above the predetermined noise threshold level. The predetermined noise threshold level may be a noise level between 70 dB and 85 dB or a noise level of 75 dB.

The detected wearer induced disturbance may be characterized as a low-level noise is indicative of a physiological noise or as a high-level noise is indicative of speech.

In yet another aspect of the invention, an earpiece system for measuring an effective sound pressure level from an ear canal of an individual is provided. The earpiece comprises a base having a canal engagement portion shaped to engage the ear canal, an outer-ear microphone positioned on the base for measuring an outer-ear sound pressure at an entrance position of the ear canal. The outer-ear microphone is configured to capture an outer-ear sound pressure at an entrance position of the ear canal and transmit the outer-ear sound pressure to a conversion module. The earpiece further comprises an in-ear microphone positioned on the base for measuring an in-ear sound pressure at an intermediate position of the ear canal, the in-ear microphone being configured to capture an in-ear sound pressure at an intermediate position of the ear canal and transmit the in-ear sound pressure to the conversion module. The earpiece further comprises the engagement portion defining a calibration conduit, the calibration conduit being configured to allow passage of sound waves from the environment through the engagement portion into the ear-canal.

The canal engagement portion may be an earplug.

The calibration conduit may be sealable with a removeable cover. The calibration conduit may be unsealed during a calibration of the earpiece and sealed during a measurement with the earpiece. The earpiece may further comprise a pivotable lever for actuating the removeable cover.

The conversion module may be configured to calculate a correction factor according to the outer-ear sound pressure and the in-ear sound pressure. The in-ear microphone may be calibrated according to the correction factor. The conversion module may calculate an effective sound pressure level according to the in-ear sound pressure and the correction factor. The effective sound pressure level may be an equivalent free field sound pressure level or an equivalent tympanic sound pressure level.

The conversion module may be configured to detect a wearer induced disturbance according to the in-ear sound pressure and the outer-ear sound pressure. The conversion module may be configured to calculate a correction factor according to the outer-ear sound pressure level and the in-ear sound pressure level or further configured to calculate the effective sound pressure level according to the measured in-ear sound pressure and the correction factor when the wearer induced disturbance is not detected.

In another aspect of the invention a method of using the earpiece for measuring an effective sound pressure level to determine a cumulative sound pressure level dosage for which the individual is exposed over a predetermined period of time is provided.

The features of the present invention which are believed to be novel are set forth with particularity in the appended claims.

BRIEF DESCRIPTION OF THE DRAWINGS

Further features and advantages of the present invention will become apparent from the following detailed description, taken in combination with the appended drawings, in which.

DETAILED DESCRIPTION

A novel method and system for measuring in-ear effective sound exposure under an earplug or without an earplug and for determining a wearer induced disturbance will be described hereinafter. Although the invention is described in terms of specific illustrative embodiment(s), it is to be understood that the embodiment(s) described herein are by way of example only and that the scope of the invention is not intended to be limited thereby.

A method and a system to calibrate and measure in-ear effective sound level exposure under a hearing protection device (HPD) such as an earplug (e.g. occluded ear) or without a HPD (e.g. unoccluded ear) will be described hereinafter. Although the system and method are described in terms of specific illustrative embodiments, it shall be understood that the embodiments described herein are by way of example only and that the scope of the device and method is not intended to be limited thereby.

Figure 1:
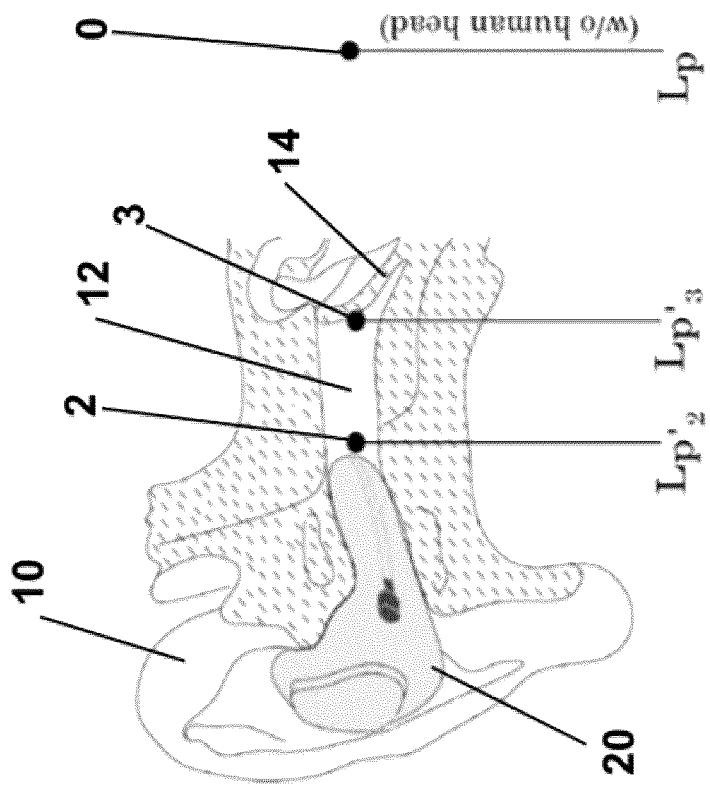
FIG. 1 presents a cross-sectional view of an ear-canal with identified sound pressure measurement positions within the ear-canal when the ear is occluded by an earplug, according to one embodiment.

Referring to FIG. 1, there is illustrated according to one embodiment, a schematic representation of the positions used to measure the sound pressure in the ear canal 12 of an occluded ear 10, such as by an earplug 21. $Lp'_2$ is the sound pressure level in the occluded ear canal 12 at an intermediate position 2 and $Lp'_3$ is the sound pressure level at the eardrum 14, such as at an eardrum position 3, when the ear canal 12 is occluded. The in-ear effective sound level exposure under a HPD is the sound pressure level at the eardrum $Lp'_3$, however $Lp'_3$ is difficult to measure since the eardrum position 3 is not easy to reach. Moreover, placing a probe in proximity of the eardrum position 3 can harm the eardrum and can also be very irritating for the wearer.

Moreover, hearing health standards normally express sound pressure level exposure in free-field sound pressure levels. The free-field sound pressure level is the sound pressure level measured outside the ear-canal. The sound pressure level measured within the ear canal must therefore be converted to a free-field sound pressure level in order to properly compare the measured levels with the hearing health standards.

According one embodiment, the sound pressure level at the eardrum $Lp'_3$, under the HPD, is estimated by measuring a sound pressure level $Lp'_2$ at the intermediate position 2 of the occluded ear canal 12 and by applying a tympanic correction factor TP-CORR to $Lp'_2$. The tympanic correction factor TP-CORR is determined according to sound pressure level measurements that are taken in an open ear or unoccluded ear, such as with the HPD removed.

According another embodiment, the sound pressure level at the eardrum $Lp'_3$, under the HPD, is estimated by measuring a sound pressure level $Lp'_2$ at the intermediate position 2 of the occluded ear canal 12 and by applying a free-field correction factor FF-CORR to $Lp'_2$. The free-field correction factor FF-CORR is determined according to sound pressure level measurements that are taken in an open ear or unoccluded ear, such as with the HPD removed.

Figure 2:
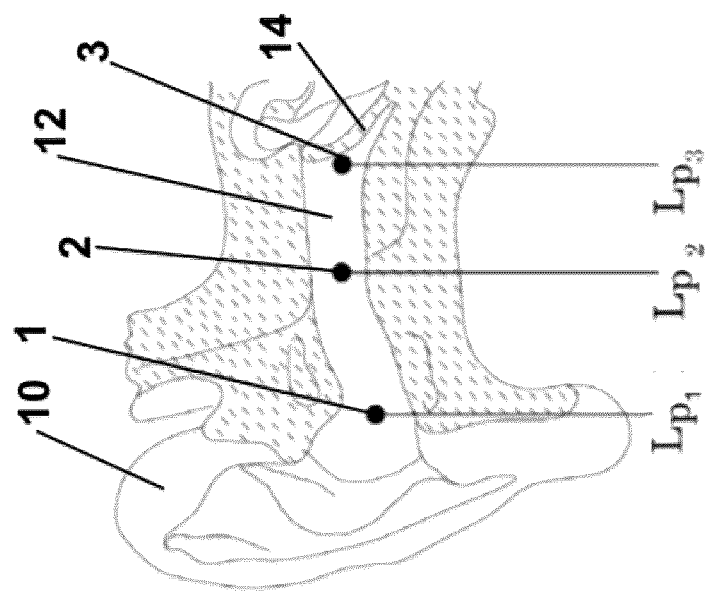
FIG. 2 presents a cross-sectional view of an ear-canal with identified sound pressure measurement positions within the ear-canal when the ear is open or unoccluded, according to one embodiment.

In FIG. 2, there is illustrated according to one embodiment, a schematic representation of the positions used to measure the sound pressure in the ear canal 12 of an open ear 10. $Lp_1$ is the sound pressure level at a canal entrance position 1 of the open ear canal 12. $Lp_2$ is the sound pressure level at the intermediate position 2 of the open ear canal 12 and $Lp_3$ is the sound pressure level at the eardrum position 3 of the open ear canal 12. Lp is the sound pressure level at a middle head position 0 that is located approximately in the middle of the head, but in absence of the human body—just as though the middle of the head were in the open.

Figure 3A:
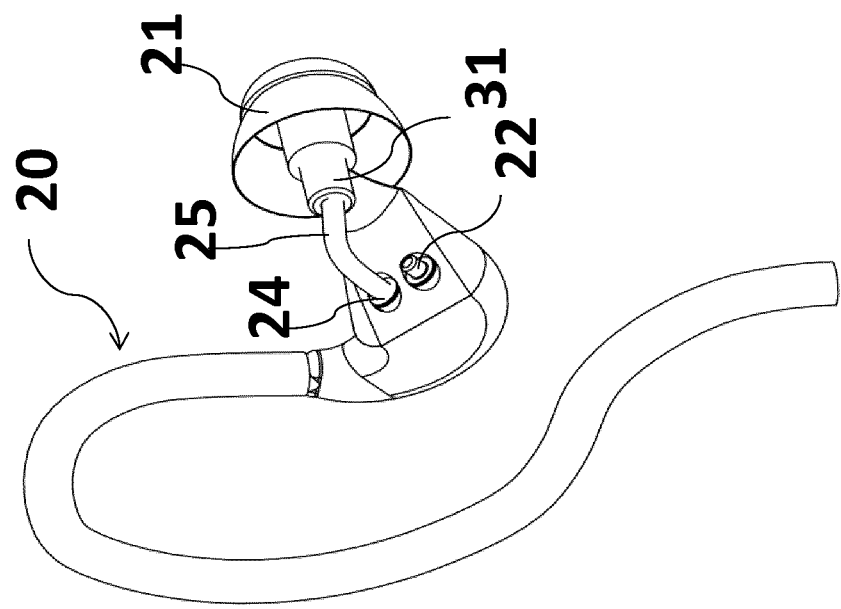
FIG. 3A presents a perspective view of a dosimetry earplug or occlusion earpiece that can be calibrated, according to one embodiment.
Figure 4A:
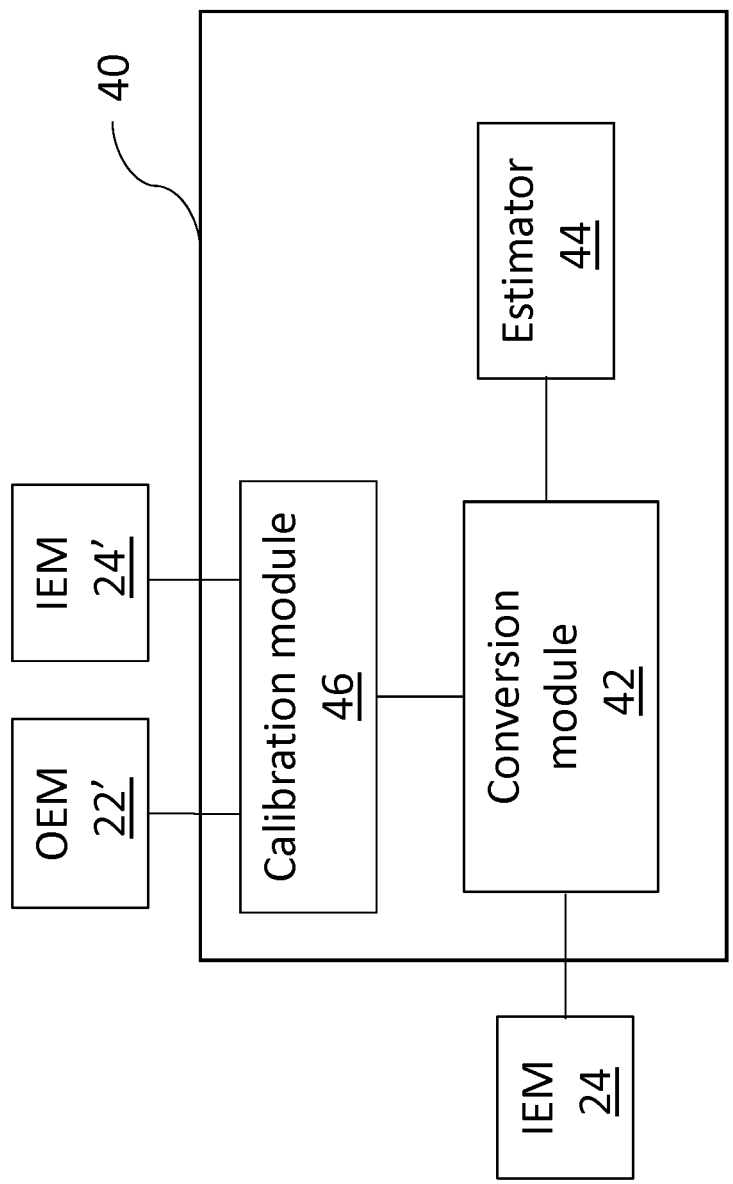
FIG. 4A presents a system for calibrating the earpieces of FIGS. 3A to 3F and providing an effective in-ear sound pressure level measurement, according to one embodiment.

Presented in FIG. 4, there is a system 40 for estimating a "free field" sound pressure level or a "tympanic" sound pressure level, according to one embodiment. The system 40 has a conversion module 42 and an estimator 44. The conversion module is adapted to receive at least an IEM 24 from the earpiece 20 of FIG. 3A for instance, and to convert the IEM 24 into a "free field" sound pressure level, such as an equivalent free field sound pressure level or into a "tympanic" sound pressure level, such as an equivalent tympanic sound pressure level. The "free field" sound pressure level or a "tympanic" sound pressure level is then processed by the estimator 44 for estimating a noise exposure dose of the wearer over a certain period of time. The conversion module 42 calculates the equivalent free field sound pressure level or the equivalent tympanic sound pressure level according to previously obtained IEM 24' sound pressure level measurements and OEM 22' sound pressure level measurements such as with the open earpiece 20'. According to one embodiment, the system 40 has a calibration module 46 adapted to receive the IEM 24' measurements and the OEM 22' measurements. According to the IEM 24' measurements and the OEM 22' measurements, the calibration module 46 calculates a free-field correction factor or a tympanic correction factor depending on the desired correction factor. The calculated correction factor is then used by the conversion module 42 to convert the IEM 24 measurement into an equivalent "free field" sound pressure level Lp or an equivalent "tympanic" sound pressure level $Lp'_3$.

Figure 3B:
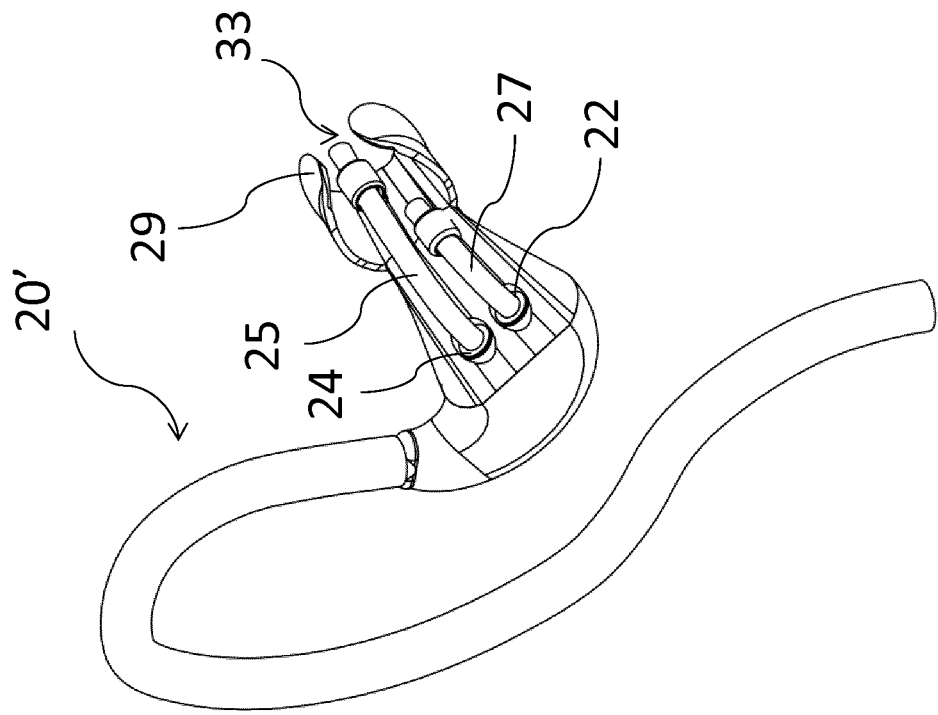
FIG. 3B is a perspective view of an open earpiece that is auto-calibratable and that can be used for calibrating the dosimetry earplug of FIG. 3A, according to one embodiment.

It shall be recognized that the IEM 24 of FIG. 4 can also be the IEM 24' of the open earpiece 20' as shown in FIG. 3B. The same correction factor FF-CORR or TP-CORR is applied to convert the measurement into an equivalent "free field" sound pressure level Lp or an equivalent "tympanic" sound pressure level $Lp_3$.

Notice that the term correction factor CORR is used to indicate either one of the free-field correction factor FF-CORR or the tympanic correction factor TP-CORR.

Various Types of Earpieces

FIGS. 3A to 3F present various types of earpieces. Each earpiece 20, 20' and 20" has an outer-ear microphone (OEM) 22 and an in-ear microphone (IEM) 24.

According to one embodiment, the earpiece 20 of FIG. 3A has an HPD such as an earplug 21. Outer-ear and in-ear sound pressure levels ($Lp'_1$ and $Lp'_2$) are captured by the microphones 22 and 24 respectively. The earpiece 20 allows to measure the effective inner-ear sound exposure under the earplug 21, such as in an occluded ear, by applying the correction factor CORR to the measured $Lp'_2$. An external microphone 22 allows to capture sound pressure outside the ear canal, such as at the entrance of the ear canal. The IEM 24 is connected to a tube or a microphonic probe 25 to capture sound pressure in the ear canal under the earplug 21 at a given point or depth of the ear canal, such as at intermediate position 2. According to one embodiment, the earplug 21 defines an adjusted passage 31 to allow insertion of the microphonic probe 25 from one extremity to the other of the earplug 21. The earpiece 20 is calibrated according to sound pressures captured by the microphones 22' and 24' of an earpiece that does not have a HPD, such as with the open earpiece 20' of FIG. 3B. The calibration allows to determine the corrections to apply to the various levels of sound pressure measured by the IEM 24, in order to convert the measured in-ear sound pressure levels into equivalent "free-field" (Lp) sound pressure levels and/or into equivalent "tympanic" ($Lp_3$) sound pressure levels.

It shall be recognized that the adjusted passage 31 can have any shape or form so long as the it is adapted to allow a transmission of captured sound pressure inside the ear canal to the IEM 24 without compromising the attenuation provided by the earplug 21 or substantially compromising the attenuation provided by the earplug 21.

It shall further be recognized that the IEM 24 can also be a miniature IEM 24 that is small enough to be positioned at a tip of the earplug 21 such as to directly capture sound pressure within the ear canal without necessitating the microphonic probe 25. In which case, the adjusted passage 31 may be shaped to allow a passage of a wire for transmitting a signal indicative of the captured sound pressure to a processor. Notice that if the miniature IEM 24 were adapted to transmit wirelessly a signal indicative of the captured sound pressure to the processor, the adjusted passage 31 may be eliminated altogether.

According to one embodiment, the earpiece 20' of FIG. 3B does not have a HPD and allows to measure effective in-ear sound exposure in an unoccluded ear. The earpiece 20' has a guide 29 that is shaped to be introduced into the ear canal and defines a passage 33 to allow sound waves of the environment to pass there through into the ear canal without obstruction. An OEM 22' allows to capture sound pressure outside the ear canal at an entry of the passage 33 (e.g. at the entry of the ear canal). An IEM 24' is connected to a microphonic probe 25 adapted to axially pass though the passage 33 to capture a sound pressure in the ear canal at a determined point or depth.

Notice that the various sound levels measured by the OEM 22' and the IEM 24' allow to calibrate not only the earpiece 20 of FIG. 3A but could also allow calibration of the open earpiece 20' itself. The calibration allows to determine the corrections to apply to the various levels of sound pressure measured by the IEM 24', in order to convert the measured in-ear sound pressure levels into equivalent "free-field" (Lp) sound pressure levels and/or into equivalent "tympanic" ($Lp_3$) sound pressure levels.

Figure 3C:
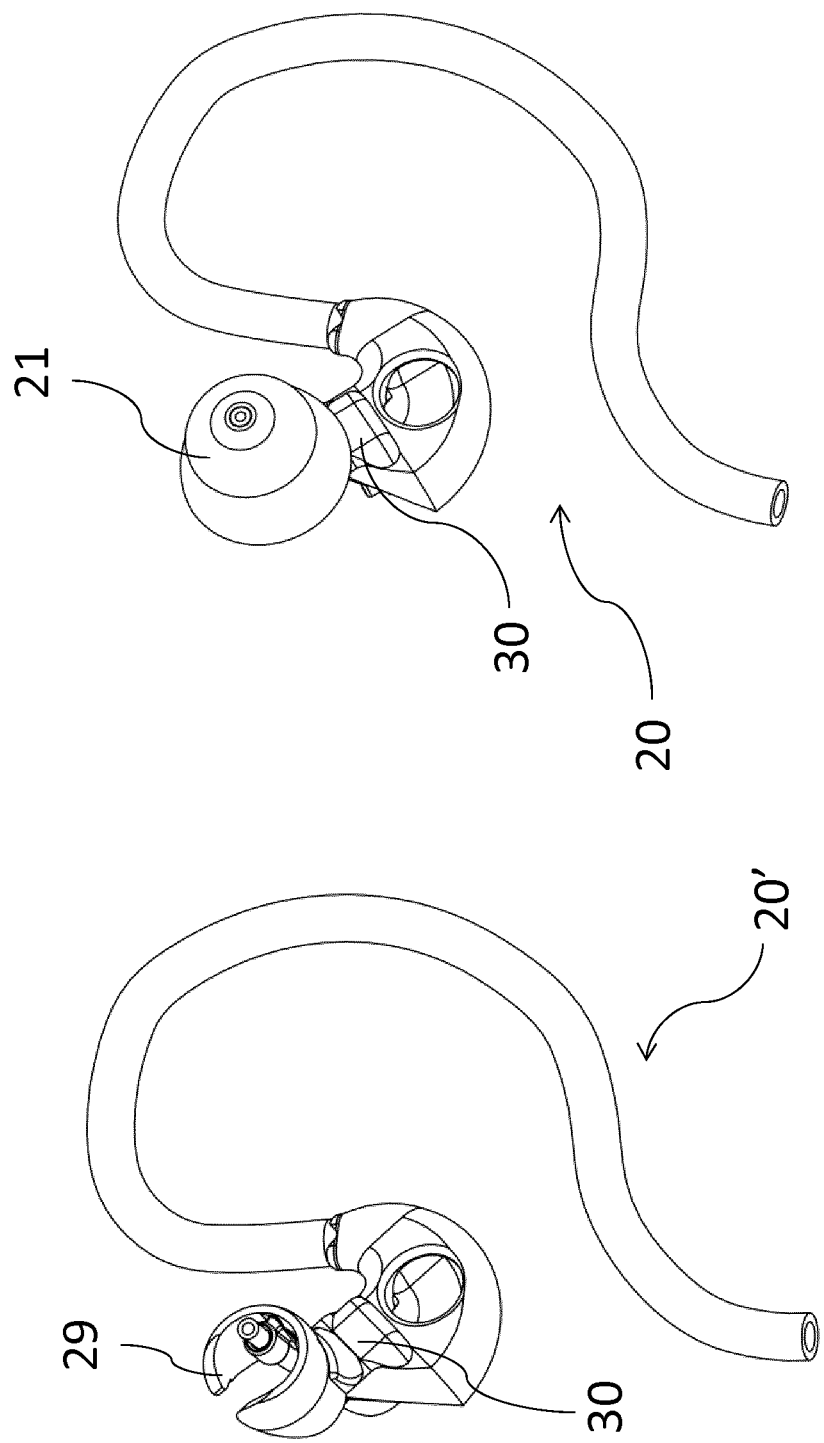
FIG. 3C presents a perspective view of the open earpiece of FIG. 3B and a perspective view of the occlusion earpiece of FIG. 3A, the earpieces have an ear abutment member to control an insertion depth of the earpiece, according to one embodiment.

According to one embodiment, as presented in FIG. 3C, the occlusion earpiece 20 of FIG. 3A and the open earpiece 20' of FIG. 3B have an abutment member 30 to ensure that the earpieces 20 and 20' are insertable into the ear canal at a same depth or to at least ensure that the IEM 24 and 24' of both earpieces 20 and 20' is positioned at a same intermediate position 2, as concurrently presented in FIGS. 1 and 2.

Figure 3D:
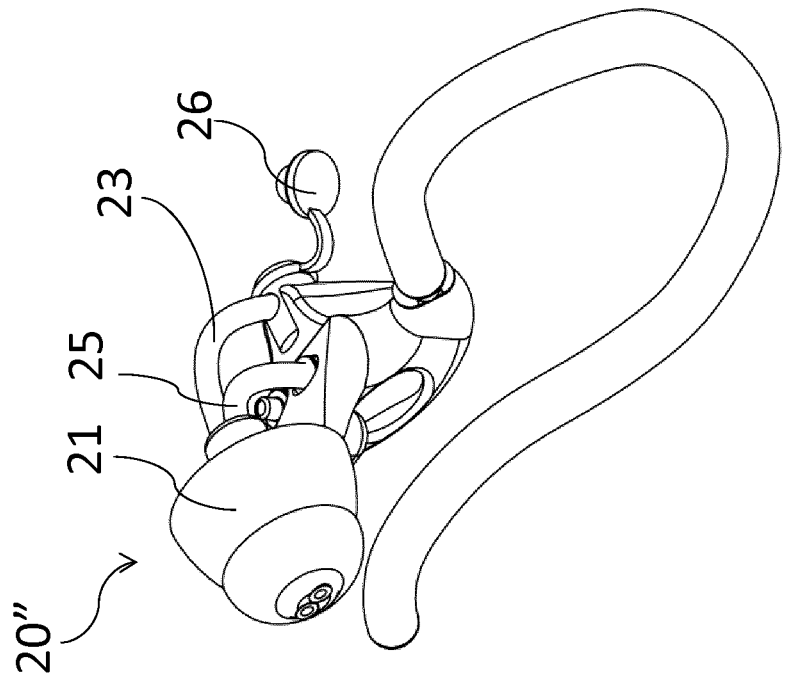
FIG. 3D presents perspective views of an occlusion earpiece having a sealable conduit with a removable cover to allow auto-calibration of the earpiece, according to one embodiment.
Figure 3D:
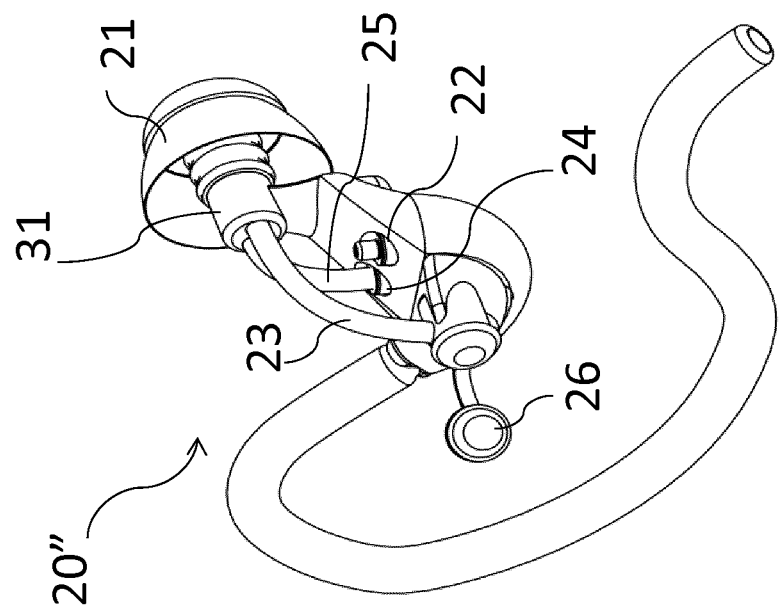

According to another embodiment as presented in FIG. 3D, there is an earpiece 20" that has an HPD such as an earplug 21. The earpiece 20" has an OEM 22" adapted to capture sound pressure outside the ear canal, such as at the canal entrance position 1. The earpiece also has an IEM 24" connected to a tube or microphonic probe 25. The IEM 24" allows to capture a sound pressure in the ear canal, under or behind the earplug 21 at a determined depth of the ear canal. According to one embodiment, the earplug 21 forms an adjusted passage 31 allowing an insertion of the microphonic probe 25 and an insertion of a sealable conduit 23 from one extremity of the earplug 21 to the other. The sealable conduit 23 can be sealed by removable cover 26. When the conduit 23 is open, the conduit 23 allows the passage of sound waves toward the ear canal via air conduction behind the earplug 21. When the conduit 23 is sealed, the external noise is attenuated by the earplug 21. According to one embodiment, the earpiece 20" has at least two functional modes, the first being a calibration mode that can be performed when the conduit 23 is open and the cover 26 is removed. When in the calibration mode, the earpiece 20" allows to determine the correction factor CORR to apply to the various sound pressure levels measured by the IEM 24" or by the IEM 24 of FIG. 3A, in order to convert the measured in-ear sound pressure levels into equivalent "free-field" (Lp) sound pressure levels and/or into equivalent "tympanic" ($Lp_3$) sound pressure levels, as explained in the following.

The second mode is a measurement mode that can be performed when the conduit 23 is closed by the cover 26. When in the measurement mode, the earpiece 20" allows to determine the effective sound exposure within the ear canal, under the earplug 21 according to the sound pressure level measurements provided by the IEM 24" and the determined correction factor CORR.

It shall be recognized that the adjusted passage 31 can have any shape or form so long as the it is capable to allow a transmission of captured sound pressure inside the ear canal to the IEM 24" and provide a sealable sound passage without compromising the attenuation of the earplug 21 or substantially compromising the attenuation of the earplug 21 when the sealable sound passage is closed.

It shall further be recognized that the IEM 24" can also be a miniature IEM 24" that is small enough to be positioned such as to directly capture sound pressure at the desired depth within the ear canal without necessitating the microphonic probe 25. In which case, the adjusted passage 31 may be shaped to allow a passage of a wire for transmitting a signal indicative of the captured sound pressure to a processor. Notice that if the miniature IEM 24" were adapted to transmit wirelessly a signal indicative of the captured sound pressure to the processor, the adjusted passage 31 would then be shaped solely as a sealable sound passage or shaped solely to provide passage of the sealable conduit 23.

According to at least one embodiment, the earpiece 20' of FIG. 3B is adapted to measure the sound pressure in the open ear canal 12. The OEM 22' has a short microphonic probe 27 to measure sound pressure levels at canal entrance position 1. The IEM 24' also has a microphonic probe 25. The microphonic probe 25 is however longer than the short microphonic probe 27 in order to allow a sound pressure measurement at the intermediate position 2. With an adequate calibration or an adequate estimation of the correction factor CORR, there is no microphone that is required to measure the sound pressure at the eardrum, such as at eardrum position 3, since the sound pressure level $Lp_3$ is estimated according to the sound pressure levels $Lp_1$ and $Lp_2$.

Determining a Free-Field Correction Factor FF-CORR

The free-field correction factor FF-CORR allows to convert an in-ear sound pressure level measurement into an equivalent free-field sound pressure level. The system and method of the present solution attempt to identify the acoustic corrections required to convert the measured in-ear sound pressure levels into equivalent "free-field" (Lp) sound pressure levels.

One of the acoustic corrections to identify is the Microphone to Eardrum Correction (MEC). With reference to FIG. 1, the MEC attempts to convert the measured sound pressure level ($Lp'_2$) into the sound pressure level ($Lp'_3$) at the eardrum when the ear canal is occluded. The relation between $Lp'_2$ and $Lp'_3$ is expressed by the following MEC equation:

$$MEC = Lp'_3 - Lp'_2$$

Another one of the acoustic corrections to identify is the Transfer Function of the Open Ear (TFOE). With reference to FIG. 2, the TFOE acoustic correction links the tympanic sound pressure level in an open ear ($Lp_3$) to the free-field sound pressure level (Lp). This relation is expressed by the following TFOE equation:

$$TFOE = Lp - Lp_3$$

A correction factor CORR is determined according to the MEC and the TFOE in order to convert the sound pressure levels ($Lp'_2$) measured under an earplug 21 within the ear-canal into an equivalent free-field sound pressure level (Lp), such as presented in FIGS. 1, 3A and 3B to 3F. The correction factor CORR is the sum of the MEC and the TFOE:

$$CORR = MEC + TFOE$$

$$CORR = Lp'_3 - Lp'_2 + Lp - Lp_3$$

According to one embodiment of the method, the acoustic impedances in the direction of the eardrum found at the intermediate position 2 and at the eardrum position 3 are not affected by the presence of the earplug 21. In other words, the transfer function relating the measured sound pressure levels $Lp'_2$ and $Lp_2$ and the measured sound pressure levels $Lp'_3$ and $Lp_3$ are similar or practically identical for an occluded ear as presented in FIG. 1 or for an open ear as presented in FIG. 2. The difference in sound pressure levels measured at the intermediate position 2 and at the eardrum position 3 be it for an occluded ear or for an open ear are practically the same, as presented by the following equation:

$$Lp'_3 - Lp'_2 \approx Lp_3 - Lp_2$$

The correction factor CORR can therefore be expressed as $Lp - Lp_2$, since:

$$CORR = Lp'_3 - Lp'_2 + Lp - Lp_3$$

$$CORR = Lp_3 - Lp_2 + Lp - Lp_3$$

$$CORR = Lp - Lp_2$$

The ratio between the sound pressure measured at the canal entrance position 1 and the sound pressure measured at any point within the ear-canal, be it in an open or occluded ear (i.e. $Lp'_2$; $Lp_2$ or $Lp'_3$; $Lp_3$), is typically independent from the incident direction of the external noise.

Figure 4B:
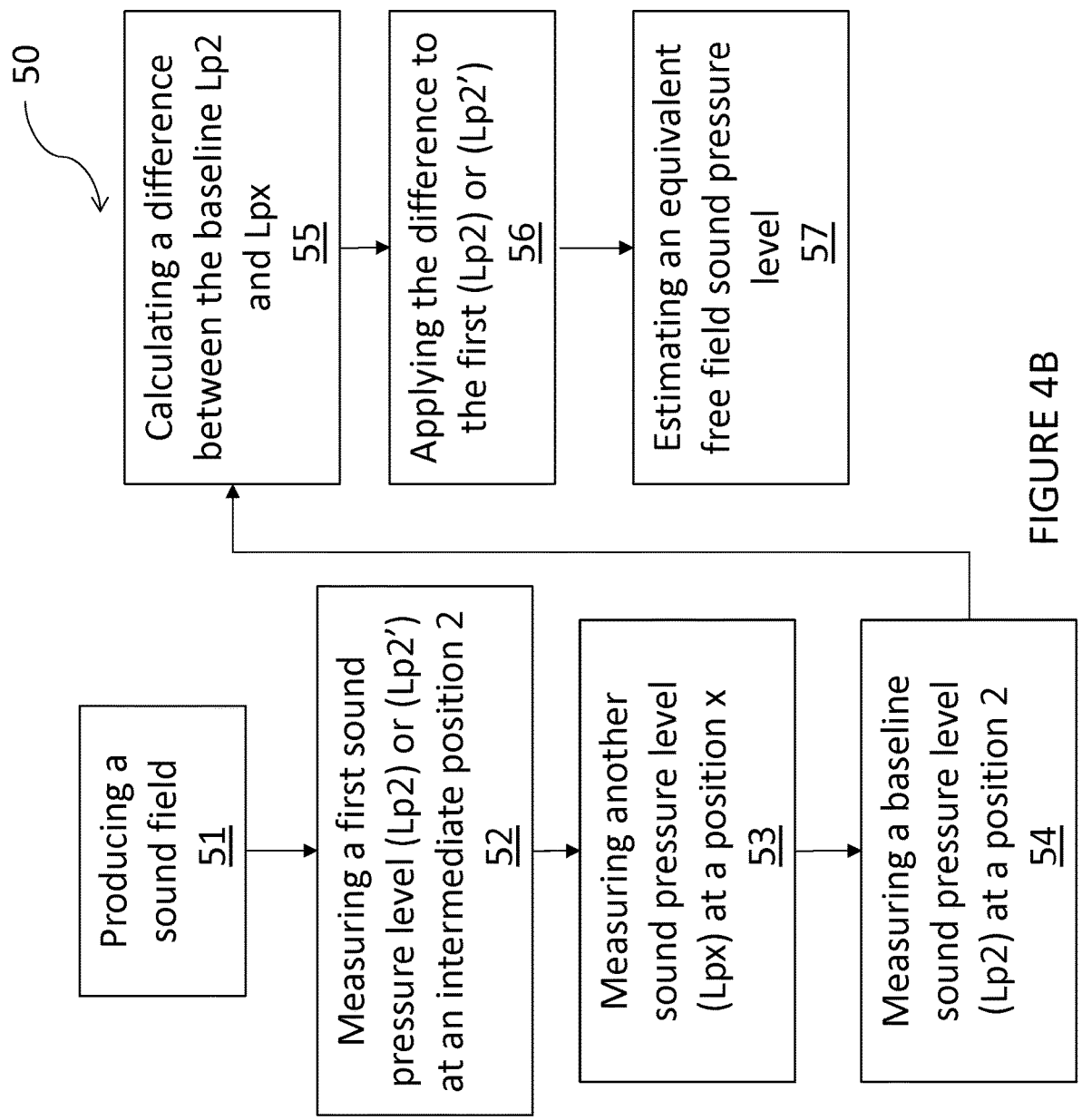
FIG. 4B presents a method for estimating an equivalent free field sound pressure level from a sound pressure level measurement captured from an intermediate position of the ear canal.

Presented in FIG. 4B, there is a method 50 for estimating an equivalent free-field sound pressure level according to a sound pressure measurement provided by the IEM 24 or IEM 24'. The method 50 includes producing a sound field in a vicinity of the wearer 51 and measuring a first sound pressure 52 at an intermediate position 2 ($Lp_2$ or $Lp_2$') and measuring another sound pressure 53 at a position x ($Lp_x$) in the presence of the sound field. The position x being located either outside the ear canal, at the canal entrance position 1 of the ear canal or upstream the intermediate position 2 such as any position located between the canal entrance position 1 and the intermediate position 2, as concurrently presented in FIG. 2. The method 50 further measuring a baseline sound pressure level 54 in an open ear at position 2 (baseline $Lp_2$) in the presence of the sound and then calculating a difference 55 between the baseline $Lp_2$ and $Lp_x$ (or baseline $Lp_2 - Lp_x$). The method 50 further includes applying the calculated difference to the first sound pressure level ($Lp_2$ or $Lp_2$') and estimating 57 the equivalent free field sound pressure level.

Figures 12A, 12B:
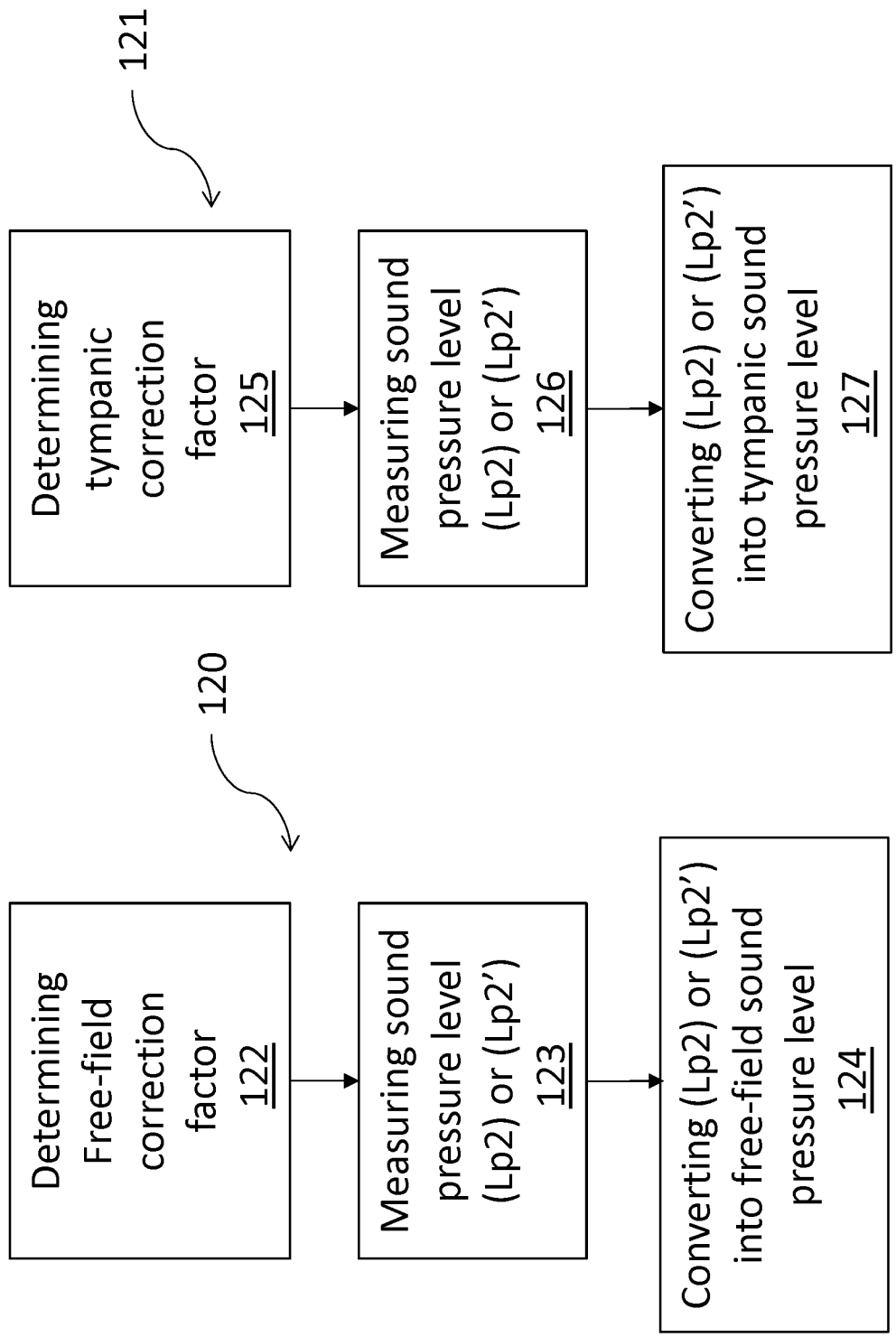
FIGS. 12A and 12B present a method for converting a sound pressure measurement captured from an ear canal into an equivalent free-field sound pressure level or into an equivalent tympanic sound pressure level, according to one embodiment.

According to one embodiment, as presented in FIG. 12A, there is a method for converting a measured sound pressure level (Lp2) or (Lp2') into an equivalent free-field sound pressure level 120. The method 120 includes determining a free-field correction factor 122, then measuring 123 a sound pressure level (Lp2) or (Lp2') and converting 124 the measured (Lp2) or (Lp2') into an equivalent free-field sound pressure level.

Determining a Tympanic Correction Factor TP-CORR

The tympanic correction factor TP-CORR allows to convert an in-ear sound pressure level measurement into an equivalent tympanic sound pressure level $Lp_3$ when the measurement is made by an open earpiece or $Lp_3$ when the measurement is made under an earplug.

According to one embodiment, there is presented a personalized calibration method for intra-auricular dosimetry. The method includes identifying the function $Lp_3 - Lp_2$, in order to determine the sound pressure levels at the eardrum. In general, the method allows to measure the sound levels within the ear canal such as $Lp_2$ and to determine a corresponding sound pressure value such as $Lp_3$ by applying the $Lp_3 - Lp_2$ function.

Figure 5:
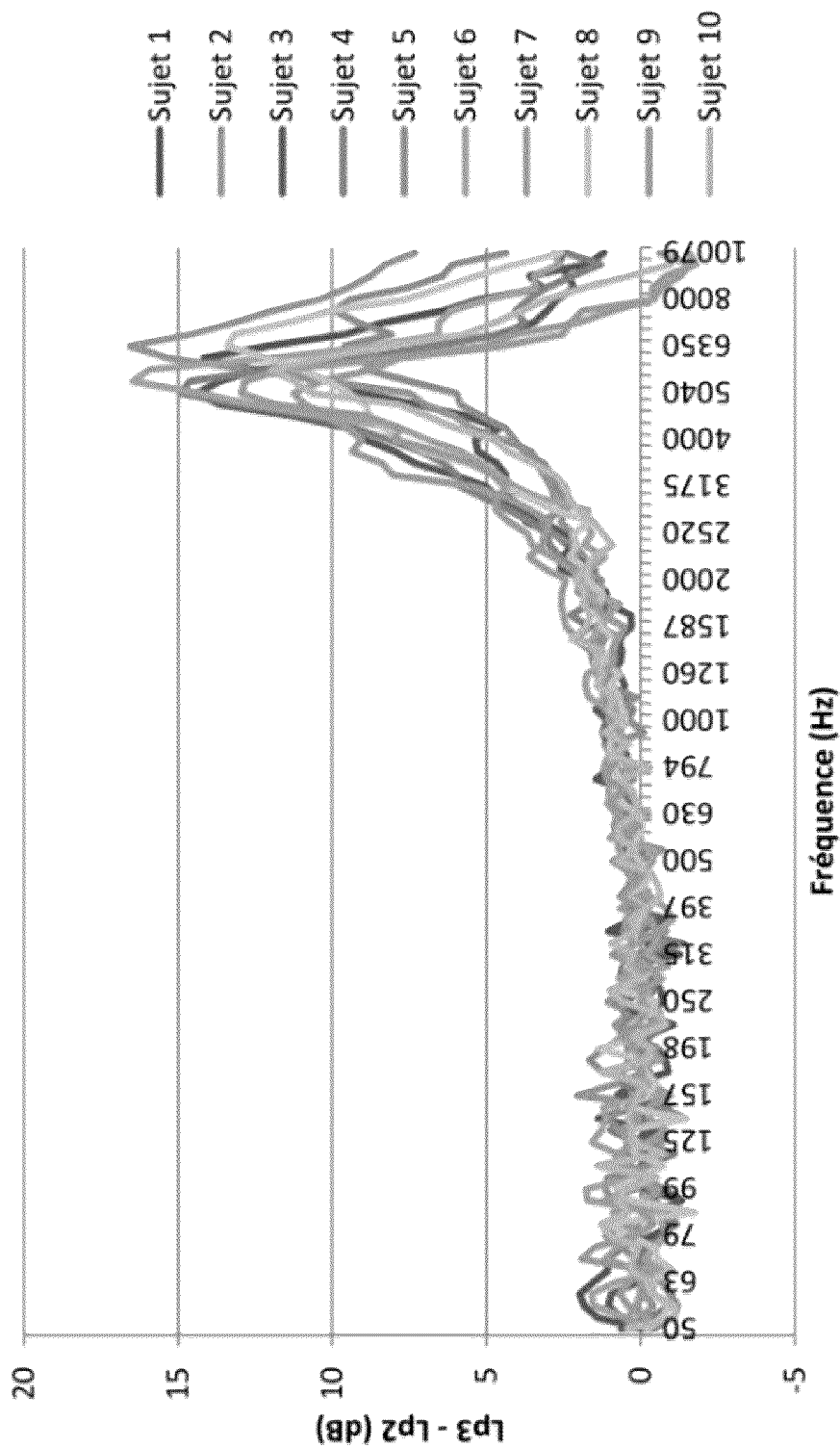
FIG. 5 presents a graph of sound level measurements taken on ten individuals, the measurements indicate the difference calculated between a sound level measured near the eardrum and a sound level measured within the ear-canal at ten millimeters (10 mm) from the ear-canal entrance ($Lp_3$–$Lp_2$) of an unoccluded ear, for each individual.

Presented in FIG. 5 is a graph depicting the difference between $Lp_3$ and $Lp_2$ measured on ten different individuals. The $Lp_2$ being measured at a depth of 10 mm from the ear canal entry in open ear (unoccluded ear). The $Lp_3 - Lp_2$ differences are presented according to various frequencies. As can be noticed, a maximum difference in dB is observable between 4500 Hz and 8000 Hz. The frequency position of the maximum difference varies depending on the distance between the measurement positions of $Lp_2$ and $Lp_3$, as concurrently presented in FIG. 2. Notice that the difference between $Lp_3$ and $Lp_2$ depends on the residual length of the ear canal that separates the intermediate position 2 and the eardrum position 3.

Figure 6:
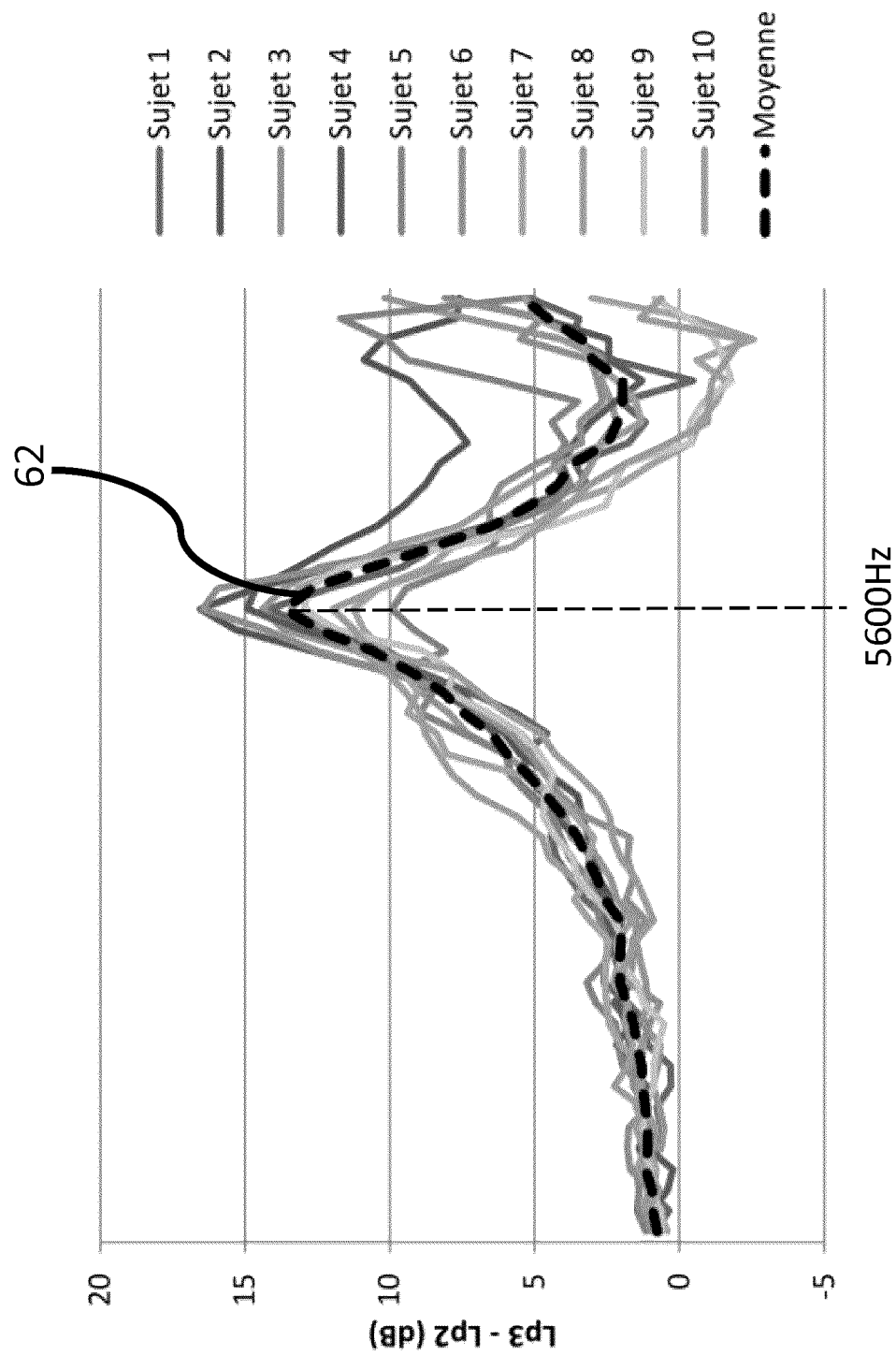
FIG. 6 presents the sound level measurements of FIG. 5 focusing on the frequency range where the measured values ($Lp_3$–$Lp_2$) vary greatly according to the frequency and reach a peak.

FIG. 6 presents an overlap (superposition) of the individual curves of FIG. 5 for the frequencies where the maximum differences ($Lp_3 - Lp_2$) are measured. As can be noticed the individual curves all present a similar profile. A dotted line curve presents the average of the overlapped curves expressed in $1/12^{th}$ octave band frequencies. According to one embodiment, the dotted line curve is a filter 62 that is used to determine the $Lp_3$.

A skilled person in the art will recognize that other filters could be extracted following a similar analysis based on another group of individuals or a larger group of individuals. The filters may vary slightly depending on the ear canal morphological parameters of the individuals analyzed. Morphological parameters may include ear canal length, ear canal geometry, presence of earwax, eardrum impedance, etc.

According to one embodiment of the method, the difference between $Lp_3$ and $Lp_2$ is estimated according to sound pressure measurements taken at two distinct positions of the ear canal. For instance, the difference between $Lp_3$ and $Lp_2$ is estimated according to a first measurement $Lp_2$ that is taken at the intermediate position 2 and a second measurement $Lp_x$ that is taken at any position upstream the first position, such as at the canal entrance position 1 of the ear canal, or at a position between the canal entrance position 1 and the in-ear position 2 or completely outside the ear canal 12, as presented in FIG. 2. The difference between $Lp_2$ and $Lp_x$ or $(Lp_2-Lp_x)$ allows to identify a standing-wave minimum or a standing-wave maximum (if the difference were expressed as $Lp_x-Lp_2$). The standing-wave minimum is typically caused by an overlapping of the incident and reflected waves within the ear canal 12. The frequency of the standing-wave minimum depends typically of the distance between the eardrum 14 and the intermediate position 2 used to measure the $Lp_2$, and is identical or at least similar to the frequency of the maximum difference corresponding to the $Lp_3-Lp_2$ function that is searched. Consequently, the difference $Lp_2-Lp_x$ can be used to estimate the frequency corresponding to the maximum difference between $Lp_3$ and $Lp_2$ (or $Lp_3-Lp_2$ function).

Figure 7:
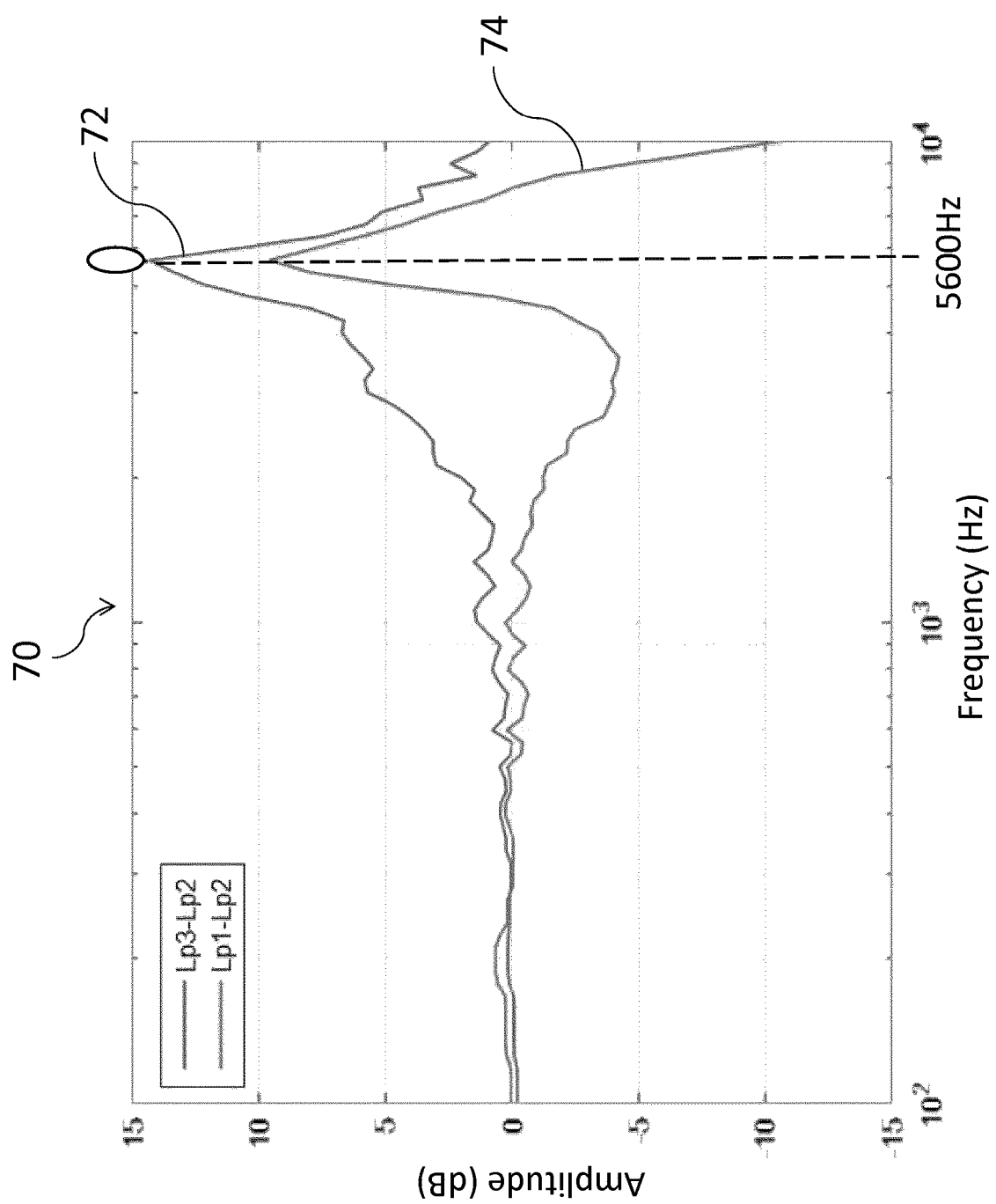
FIG. 7 presents sound level measurements taken from an unoccluded ear of an individual according to functions $Lp_1$–$Lp_2$ and $Lp_3$–$Lp_2$ over a range of frequencies, where the sound level measurements taken at $Lp_1$ are at the ear-canal entrance, at $Lp_2$ are within the ear-canal at eight millimeters (8 mm) from $Lp_1$ and at $Lp_3$ are in proximity of the eardrum.

For instance, FIG. 7 presents a graph 70 having function $Lp_1-Lp_2$ identified as curve 74 and function $Lp_3-Lp_2$ identified as curve 72 measured in a same individual where the $Lp_2$ is measured at an ear-canal depth of 8 mm and the $Lp_1$ is measured at the entry of the ear canal. The standing-wave minimum of the functions $Lp_1-Lp_2$ as shown by curve 74 is at around 5600 Hz and the maximum difference between $Lp_3$ and $Lp_2$, as shown by curve 72, corresponds to a frequency that is also around 5600 Hz.

Figure 8:
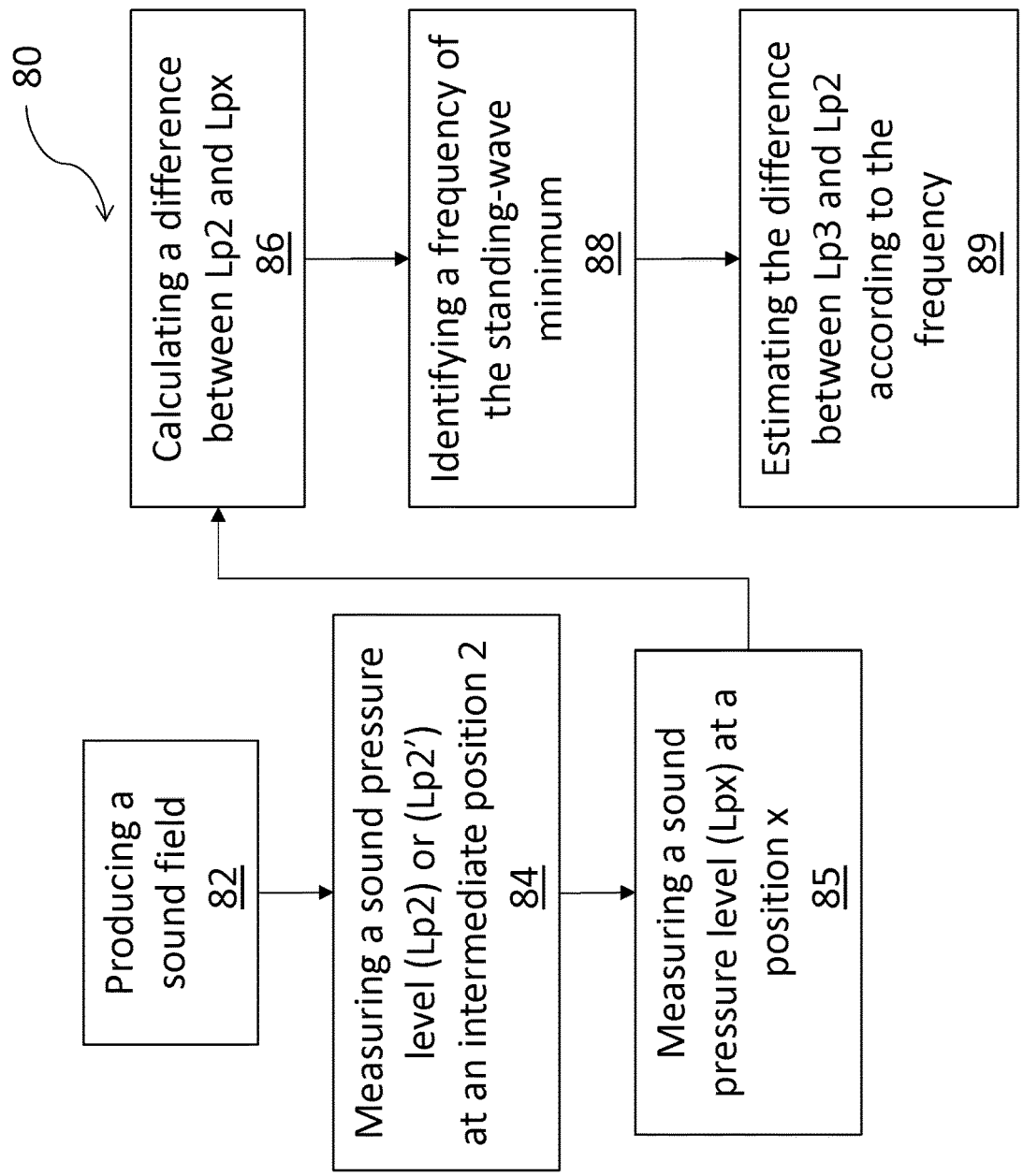
FIG. 8 presents a method for estimating an equivalent tympanic sound pressure level from a sound pressure level measurement captured from an intermediate position of the ear canal.

Referring now to FIG. 8, there is a method 80 for determining the $Lp_3-Lp_2$ function in order to estimate the sound level at the eardrum according to $Lp_2$ and $Lp_x$. The method includes producing a sound field in a vicinity of the wearer 82 and measuring a first sound pressure 84 at an intermediate position 2 and measuring a second sound pressure 85 at a position x in the presence of the sound field. The position x being located either outside the ear canal, at the canal entrance position 1 of the ear canal or upstream the intermediate position 2 such as any position located between the canal entrance position 1 and the intermediate position 2, as concurrently presented in FIG. 2. The method further includes calculating a difference between $Lp_2$ and $Lp_x$ 86 (or $Lp_2-Lp_x$). Identifying a frequency 88 corresponding to a standing-wave minimum according to the calculated difference between $Lp_2$ and $Lp_x$. Estimating 89 the $Lp_3-Lp_2$ according to the identified frequency.

The sound field produced 82 is a sound field produced by a sound source such as a speaker that is directed towards the wearer and is preferably a sound field that covers or sweeps all frequencies in a frequency range of interest such as typically a frequency range that is between 50 Hz and 10 kHz. Moreover, the sound level of the of the sound field shall be sufficiently high and may be greater than the sound level of physiological noises normally produced by the wearer, such as breathing sound level, heartbeat sound level, etc. According to one embodiment, the sound field is a white noise. According to another embodiment, the sound field is a sine sweep.

The first sound pressure is measured 84 at the intermediate position 2 or 2' is preferably measured at midway between the eardrum and the ear canal entry or at any predetermined depth from the ear canal entry. The second sound pressure is measured 105 is preferably measured at a position that is located between the sound source and the head of the wearer. Notice that this second sound pressure measurement can be performed in the presence or in the absence of the wearer.

The difference between $Lp_2$ and $Lp_x$ can be calculated 86 by calculating the pressure ratio $Lp_2/Lp_x$ expressed in decibels.

According to one embodiment, the estimation 89 of the difference between $Lp_3$ and $Lp_2$ is performed according to a predetermined average filter such as the filter depicted as a dotted line curve in the graph of FIG. 6. The filter is normally established according to measurements performed on a several individuals. The predetermined average filter should ideally be frequentially centered such as to substantially have a maximum that corresponds to the identified standing-wave minimum 88.

According to one embodiment, the method 80 allows to calibrate an earpiece by using an "open" dosimetry earpiece such as the earpiece 20' of FIG. 3B. As can be noticed, that earpiece 20' does not provide an attenuation and the correction $Lp_3-Lp_2$ allows to convert a sound pressure level measured within the ear-canal into a sound pressure level at the eardrum for a given wearer. Considering that the "open" dosimetry earpiece 20' has the IEM 24' that is adapted to measure a sound pressure at the intermediate position 2, the estimated correction $Lp_3-Lp_2$ can to be applied to the sound pressure measurements provided for instance by the IEM 24 of the occluding earpiece 20 of FIG. 3A, since the IEM 24 of the earpiece 20 measures a sound pressure at sensibly the same intermediate position 2.

According to another embodiment, the calibration method 80 is performed by using the dosimetry earpiece 20" adapted to provide an attenuation to the wearer with earplug 21 having the OEM 22", the IEM 24" and the sealable conduit 23 that can be opened when used in the calibration mode and closed when used in the dosimetry mode. The sealable conduit 23 being sealed by the removable cover 26. The calibration can thereby be performed without removing the earpiece 20" and calibration may be performed on the fly or in real time. Moreover, the distance between the intermediate position 2 and the eardrum position 3 is ensured to be the same during the calibration as well as during the dosimetry measurements and the correction function $Lp_3-Lp_2$ to be applied to the IEM measurements are ensured to be accurate while performing dosimetry measurements.

According to one embodiment, as presented in FIG. 12B, there is a method for converting a measured sound pressure level $(Lp_2)$ or $(Lp_2')$ into an equivalent tympanic sound pressure level 121. The method 121 includes determining a tympanic correction factor 125, then measuring 126 a sound pressure level $(Lp_2)$ or $(Lp_2')$ and converting 127 the measured $(Lp_2)$ or $(Lp_2')$ into an equivalent tympanic sound pressure level.

Determining Wearer-Induced-Disturbances (WIDs)

When the ear is occluded such as in FIG. 1, the sound pressure levels can be increased considerably when the wearer or user produces noise of his own such as speech, cough, chewing, walking noises, etc. Such noises are referred to as wearer-induced-disturbances (WIDs). Certain acoustic reflexes, such as the stapedius reflex are thought to allow the human ear to protect itself from noises produced by himself. It is therefore important to be able to dissociate, when measuring the noise dose under the HPD, the sound contribution produced by the wearer himself and the sound contribution produced in the environment. Unfortunately, conventional in-ear dosimetry devices do not allow to dissociate the WIDs from sounds produced in the environment.

According to one embodiment, the method and system allows to distinguish the noises produced by the wearer (WIDs). The IEM 24 of an earpiece such as the earpiece 20 of FIG. 3A is adapted to measure a noise dose to which the wearer is exposed, however depending on the origin of the noise the measurements provided by the IEM 24 can be ignored to provide an accurate of assessment of the noise exposure. The origin of the noise can either be a wearer induced noise (WID) or an environment noise and is determined according to the measurements provided by the OEM 22 and the IEM 24 In some embodiments, the system is adapted to detect noises produced by the wearer by comparing the OEM 22 measurement with the IEM 24 measurements. The comparison can be performed in real-time or following the recording of measurements provided by the OEM 22 and the IEM 24. Notice however that the detection of WIDs can be performed according to various detection methods.

A First Method for Detecting WIDs

According to one embodiment, the earpiece 20 is adapted to transfer the OEM and IEM measurements to a processor, such as a Digital Signal Processor (DSP). The processor allows to compare and process the signals captured by the OEM 22 and the IEM 24, according to the following method.

In general, according to one embodiment of the WIDs detection method 40, two transfer functions H1 and H2 are determined 42 according to signals captured by the OEM 22 and the IEM 24, a detected value $\Delta$ is calculated 44 according to the two transfer functions and the detected value $\Delta$ is compared 46 to a WIDs detection threshold $\Delta_s$ in order to detect a WID 48.

The two transfer functions H1 and H2 are determined according to the signals captured by the OEM 22 and the signals captured by the IEM 24. For instance, the transfer functions H1 and H2 are determined according to an inter-spectrum $G_{xy}$ between the two measurements provided by the OEM 22 and the IEM 24. The transfer functions H1 and H2 are further determined according to autospectrum $G_{xx}$ and $G_{yy}$ of the external signals measured by the OEM 22 and internal signals measured by the IEM 24, respectively.

$$H_1(f) = \frac{G_{xy}(f)}{G_{xx}(f)} \text{ et } H_2(f) = \frac{G_{yy}(f)}{G_{xy}(f)}$$

The detected value $\Delta$ is calculated according to an average ratio in dB between the transfer functions $H_1$ and $H_2$ for frequencies between $f_{min}$ and $f_{max}$. Notice that the $\Delta$ is calculated for a predetermined duration, such as one second. For instance, $\Delta$ is calculated by using the following equation:

$$\Delta = \frac{\sum_{f_i=f_{min}}^{f_N=f_{max}} 20\log\left(\frac{H_2(f_i)}{H_1(f_i)}\right)}{N}$$

N being the number of frequency bands.

The WIDs detection threshold $\Delta_s$ is indicative of the detected values $\Delta$ above which the corresponding measured signals by the OEM 22 and the IEM 24 are considered to be polluted by a WID, such as speech. When the detected value $\Delta$ is below the threshold value $\Delta_s$ ($\Delta<\Delta_s$), the method considers that there are no WIDs. When the detected value $\Delta$ is greater than the threshold value $\Delta_s$ ($\Delta>\Delta_s$), the method 40 detects a WID.

According to one embodiment, the method 40 further verifies 49 the noise type or if the WID is caused by a noise level produced by the wearer that is high or low. If the noise level produced by the wearer is low, the method 40 can determine that the signal measured by the OEM 22 is not impacted by the WID and can be used to estimate the in-ear noise levels. For instance, physiological noise types (ex. swallowing, chewing, heartbeat, breathing etc.) produce in general a noise level that is low and do not influence the signal measured by the OEM 22.

In order to determine the type of noise influencing the detected value $\Delta$, a noise level threshold value $Lp_s$ is defined. This threshold value $Lp_s$ can be determined based on sound pressure levels comparison between measurements taken when a wearer is talking or not talking, for instance. The $Lp_s$ value can be defined for sound pressure levels captured by either the OEM 22 or the IEM 24. The following table presents an example of the decision process used to detect speech produced by the wearer, according to one embodiment:

|  | $Lp'_2 > Lp_s$ | $Lp'_2 < Lp_s$ |
| --- | --- | --- |
| $\Delta < \Delta_s$ | No WIDs detected | No WIDs detected |
| $\Delta > \Delta_s$ | High-level noise WIDs detected (such as speech) | Low-level noise WIDs detected (such as breathing noise) |

According to the decision process, when $\Delta>\Delta_s$ and $Lp'_2>Lp_s$, the method 40 detects high-level noise WIDs and ignores the signals measured by the OEM 22 and the IEM 24. When the $\Delta>\Delta_s$ and $Lp'_2<Lp_s$ low-level noise WIDs are detected and the method ignores only the signals measured by the IEM 24, the OEM 22 signals can be used to estimate the in-ear noise level. However, when the $\Delta<\Delta_s$, no WIDs are detected and the signal measured by the IEM 24 can be used for estimation of the in-ear noise levels.

According to one embodiment, the method 40 is further adapted to determine the sound exposure level $Lp_{exp}$ of the wearer. The sound exposure level $Lp_{exp}$ is any in-ear noise exposure levels that are captured in absence of a high-level noise WIDs, such as when: $\Delta<\Delta_s$ and/or $Lp'_2<Lp_s$.

Several methods allow to calculate the $Lp_{exp}$ level. In certain embodiments, the $Lp_{exp}$ is calculated based on the autospectrum measurement of the IEM 24. In which case the $Lp_{exp}$ level is determined according to the following equation:

$$Lp_{exp} = Lp'_2$$

In other embodiments, the $Lp_{exp}$ level is calculated based on the correlated power of the IEM 24. In which case the $Lp_{exp}$ level is determined according to the following equation:

$$Lp_{exp} = Lp'_2 + 10\log_{10}(\gamma)$$

$$\text{where: } \gamma(f) = \frac{|G_{xy}(f)|^2}{G_{xx}(f) \cdot G_{yy}(f)} = \frac{H_1(f)}{H_2(f)}.$$

The calculation of the $Lp_{exp}$ based on the correlated power of the IEM 24 as compared to the OEM 24 allows to exclude or at least reduce the impact of non-correlated noises, such as when: $\Delta>\Delta_s$ and/or $Lp'_2<Lp_s$. Non-correlated noises are captured noises that have a very low influence on the noises captured by the OEM 22. In fact, the non-correlated noises are typically physiological noises produced by the wearer, such as breathing, swallowing, sneezing and even walking, rubbing of wires on clothing or movements involving facial contact.

According to one embodiment, the earpiece 20 is adapted to transfer the OEM and IEM measurements to a processor, such as a Digital Signal Processor (DSP). The processor allows to compare and process the signals captured by the OEM 22 and the IEM 24, according to the following method.

Second Method for Detecting WIDS

In another embodiment, the correlation between two signals at specific frequencies is the coherence function γ2. It is defined as:

$$\gamma^2(f) = \frac{|S_{OI}(f)|^2}{S_{OO}(f)S_{II}(f)} \quad (1)$$

where $S_{OO}(f)$ is the autospectrum of the time signal o(t) measured by the OEM 22, $S_{II}(f)$ is the autospectrum of the time signal i(t) measured by the IEM 24, and $S_{OI}(f)$ is the cross spectrum between the two signals o(t) and i(t). Coherence $\gamma^2(f)$ measures the degree of linear relationship between the two signals at any given frequency or band center frequency, on a scale from 0 (o(t) and i(t) are uncorrelated) to 1 (o(t) and i(t) are fully correlated).

For a given time-frame i, it is possible to calculate the coherence function at specific frequencies and to average it across the desired frequency range. This gives the amount $\Delta_i$, a mean coherence function expressed in dB as follows:

$$\Delta_i = -10\log_{10}\left(\frac{\sum_{f_p=f_{min}}^{f_p=f_{max}} \gamma_i^2(f_p)}{N}\right) \quad (2)$$

where fmin and fmax are the lowest and highest bands of the desired frequency range to be determined, and N is the number of frequency bands within this range. The mean coherence function $\Delta_i$ is a positive number expressed in dB and approaches 0 when the two microphone signals are highly coherent between fmin and fmax, over the time frame i. The values of fmin and fmax are indicative of the disturbance signals to be detected (e.g., speech, coughing, sneezing, walking, etc.). According to one embodiment, the Eqs. (1) and (2) are implemented as fractional band calculations, since computing $\Delta$ from narrow band values can decrease performance as it can give too much weight to higher frequencies.

According to one embodiment, the mean coherence function $\Delta$ is computed for every time frame of duration $\Delta T$ (e.g., at every 0.5 s), and compared to a threshold value $\Delta_{th}$ above which it is assumed a substantial part of the signal measured by the IEM consists of noise contributions from the wearer. When $\Delta_i<\Delta_{th}$, the impact of WIDs on the sound pressure received by the IEM 24 is negligible, which implies that:

$$L_{IEM,i}*(f)\approx L_{IEM,i}(f) \quad (3)$$

where $L_{IEM,i}(f)$ is the sound pressure level (SPL), such as $Lp_2'$ measured inside the occluded ear during time frame i, and $L_{IEM,i}*(f)$ is the SPL that would be measured in the absence of WIDs.

When $\Delta_i>\Delta_{th}$, the SPL that would be measured in the absence of WIDs ($L_{IEM,i}*(f)$) can be estimated using two different methods.

Method 1): Assuming that the Earplug Attenuation Remains Constant During WIDs

A first method of estimating the SPL that would be measured in absence of WIDs involves computing the $L_{IEM,i}*(f)$ by assuming that the earplug attenuation remains constant during WIDs:

$$L_{IEM,i}*(f)\approx L_{OEM,i}(f)-NR_{tmp}(f) \quad (4)$$

where $L_{OEM,i}(f)$ is the SPL measured by the OEM during time frame i, $NR_{tmp}(f)$ is the estimated noise reduction (SPL difference between OEM and IEM) measured when the "$\Delta<\Delta_{th}$" condition was last met, i.e. the last time no WIDs were detected. This approach is particularly adapted for WIDs that increase the SPL inside the ear but barely make any difference to the sound pressure measured outside the ear by the OEM 22. This method is better adapted for low to medium noise environments, as such WIDs, hereafter referred to as "low-level WIDs", typically hardly contribute to the IEM's 24 signal in high noise environments.

Method 2a) Assuming Ambient Noise Levels Remain Constant

A second method of estimating that SPL that would be measured in absence of WIDs involves computing the $L_{IEM,i}*(f)$ by assuming that the ambient noise levels remain constant during WIDs:

$$L_{IEM,i}*(f)\approx L_{tmp}(f) \quad (5)$$

where $L_{tmp}(f)$ is the SPL measured by the IEM 24 when the "$\Delta<\Delta_{th}$" condition was last met, i.e. the last time no WIDs were detected. This approach is particularly suited for WIDs that significantly affect the levels measured by the OEM 22. Such WIDs, hereafter referred to as "high-level WIDs", include all vocal WIDs (speech, cough, throat clearing, etc.) and other WIDs to be defined. This method is not adapted to low noise environments in which the wearer's physiological noise (breathing, heartbeats, etc.) contribute continuously to the sound pressure inside the ear canal, hence making it difficult to meet the "$\Delta<\Delta_{th}$" criterion even for short periods of time.

Method 2b): Assuming Ambient Noise Levels Remain Constant

Notice that the $L_{IEM,i}*(f)$ can be approximated as being the same as when the "$\Delta<\Delta_{th}$" condition was last met, or when $L_{IEM}*(f)$ was last estimated using Eq. (4), because the $\Delta_{th}$ value was exceeded due to low-level WIDs. This method is simply a variation of method (2a) when the latter is used together with method (1).

Combined Method 1) and 2b)

According to one embodiment, the $L_{IEM,i}*(f)$ is calculated according to both methods (i.e. Assuming that the earplug attenuation remains constant during WIDs and Assuming that ambient noise levels remain constant). The two methods can be used together as each is adapted to a specific type of WIDs, which implies that a strategy should be found to distinguish low-level WIDs from high-level WIDs. A characteristic that can help to distinguish between the two types of WIDs levels is the in-ear SPLs generated by the corresponding signals. Indeed, high-level WIDs such as speech are likely to generate higher in-ear SPLs than low-level (and non-vocal) WIDs. Hence, one way to distinguish high-level WIDs from low-level WIDs is to consider a threshold level $L_{th}$ below which no high-level WIDs can theoretically occur. The in-ear SPL in the frequency range of interest is defined as:

$$L_i = 10\log_{10}\left(\sum_{f_p=f_{min}}^{f_p=f_{max}} 10^{\frac{L_{IEM,i}(f_p)}{10}}\right) \quad (6)$$

To be consistent with Eq. (2), the in-ear SPLs and threshold value $L_{th}$ are compared within the same frequency range used to calculate the mean coherence function $\Delta(f_{min} < f < f_{max})$. Whenever $L_i > L_{th}$, any detected WID is considered as "high-level" (i.e. having a significant impact on $L_{OEM,i}(f)$), which implies that method (2b) should be used rather than method (1). Finally, method (2b) requires a prior knowledge of $L_{tmp}(f)$ and $NR_{tmp}(f)$, which implies that the "$\Delta < \Delta_{th}$" criterion should be met beforehand. When WIDs are detected ($\Delta > \Delta_{th}$) and the variables $L_{tmp}(f)$ and $NR_{tmp}(f)$ are not yet initialized, $L_{IEM,i}*(f)$ can be estimated using the following expression:

$$L_{IEM,i}*(f) \approx L_{IEM,i}(f) + 10\log_{10}(\gamma_i^2(f)) \quad (7)$$

where the quantity $-10\log_{10}(\gamma^2(f))$ represents the estimated noise contribution, in dB, from the portion of the signal that is uncorrelated with the signal measured by the OEM 24.

Figure 9:
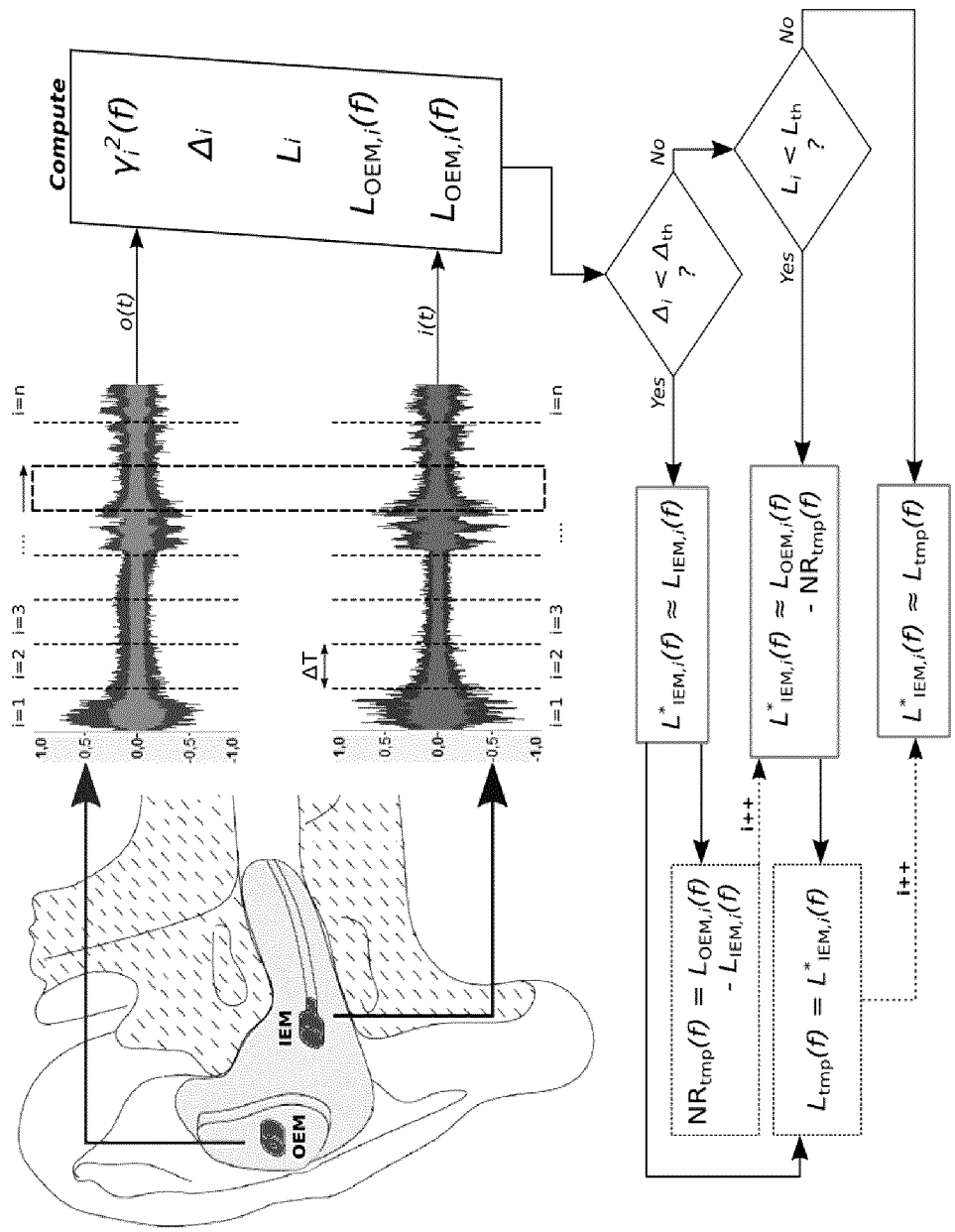
FIG. 9 presents a method for detecting wearer induced disturbances (WIDs), according to one embodiment.

The suggested overall methodology is summarized in FIG. 9.

According to one embodiment, the sound level exposure $Lp_{exp}$ is directly calculated according to an autospectrum of the IEM 24 or according to a correlated power of the IEM 24.

Detection of WIDs in a Strong Noise Environment

Figure 10:
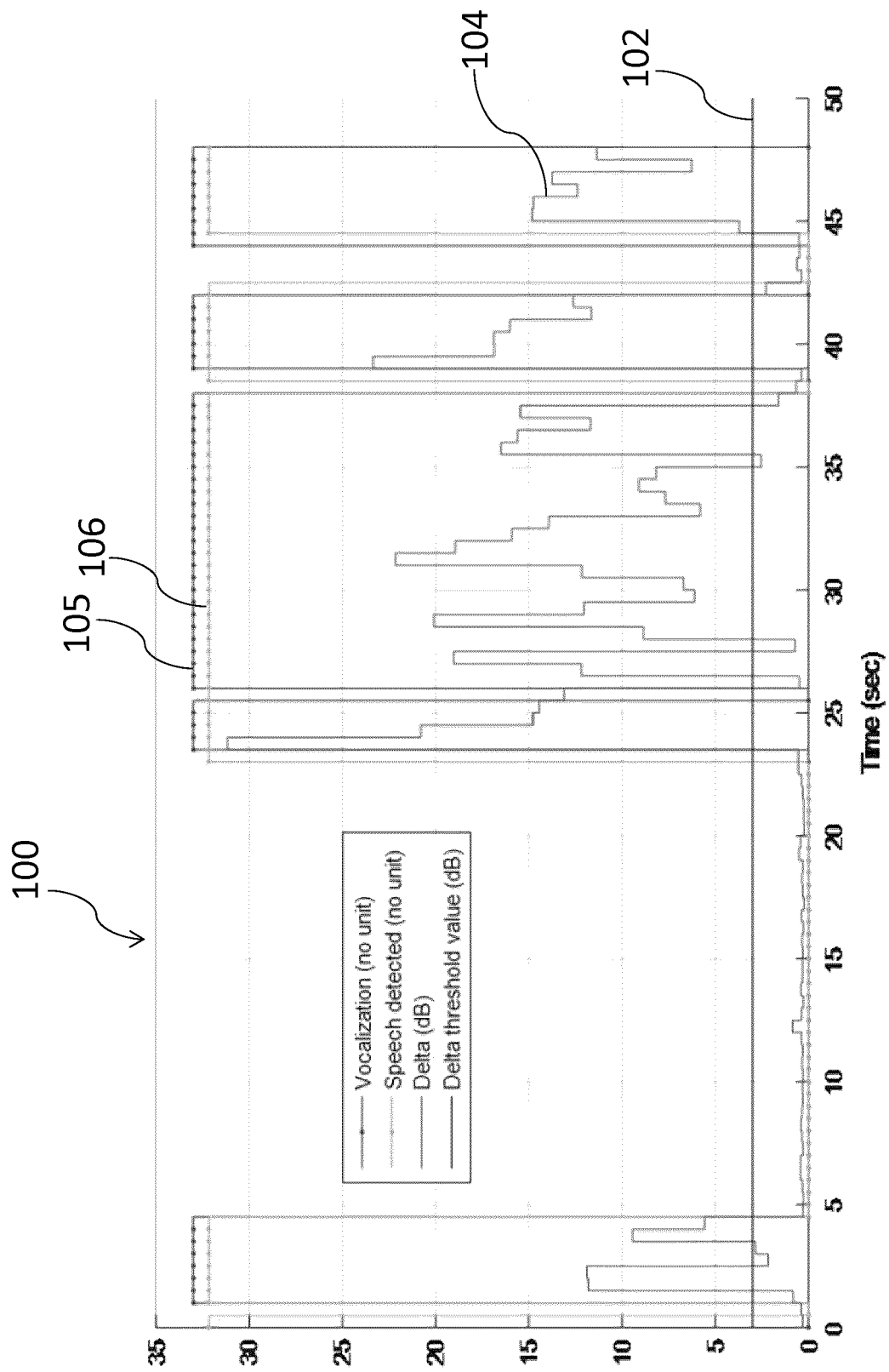
FIG. 10 presents a graph of detectable events expressed in Delta (Δ) value or DB during a period of time as an individual is speaking while in a strong noise environment.

Presented in FIG. 10 is a graph of detectable events expressed in Delta ($\Delta$) value or DB during a period of time as an individual is speaking while in a strong noise environment, as referenced as curve 104. As can be noticed, a detection threshold ($\Delta_s$), referenced as line 102, is set to 3 dB and any event that has an associated Delta ($\Delta$) value that is greater than the detection threshold ($\Delta_s$) is considered as a WID by speech, as referenced as curve 106. Notice that that a sliding average "immediate neighbor" was applied to the values of the graph to ignore outstanding values. The detected speech events correspond sensibly to the monitored vocalization (speech produced by the wearer) time periods, as referenced as curve 105.

FIG. 100 presents results obtained with a detection threshold $\Delta_s$ of 3 dB, a temporal step of 0.5 seconds, a minimum frequency $f_{min}$ of 500 Hz, a maximum frequency $f_{max}$ of 1000 Hz and a sound level threshold $Lp_s$ for the IEM of 70 dBA.

It shall be recognized that although the example of FIG. 10 is directed to the detection of speech as a WID, any other type of WID or combination of WIDs could be detected by the method. Associated detection thresholds $\Delta s$, temporal step, minimum frequency and maximum frequency can be set according to the type of WID to be detected. Moreover, the sound level threshold $Lp_s$ for the IEM can also be set according to the type of WID to be detected. In some cases, various groups of detection parameters can be set to individually detect several types of WIDs. In other cases, a single group of detection parameters can be set to detect several types of WIDs, in general. For instance, the sound level threshold $Lp_s$ for the IEM can be any sound level that is in the range between 65 dBA and 85 dBA, such as 75 dBA According to one embodiment, the ambient noise produced in the environment of the wearer is used to perform the calibration of the earpiece 20". That is, the acoustic corrections $Lp_3$–$Lp_2$ and/or $Lp$–$Lp_2$ are estimated using the ambient noise as a sound source. According to one calibration method, before measuring the $Lp_x$ and the $Lp_2$, the method includes verifying that a sufficient number of frequencies are available in the ambient noise to perform calibration. For instance, calibration may be performed only if the $\Delta < \Delta_s$, and the sound level measure by the OEM 22" is greater than 50 dB for all the frequencies of interest.

According to yet another embodiment, the calibration method is performed automatically and repetitively at a predetermined interval. In such embodiment, the earpiece 20" or a controller of the earpiece 20" is configured to continuously or a periodically update of the $Lp_3$–$Lp_2$ correction function. Such automated calibration would not require an intervention of the wearer or would only require a minimal intervention by the wearer.

Figure 11:
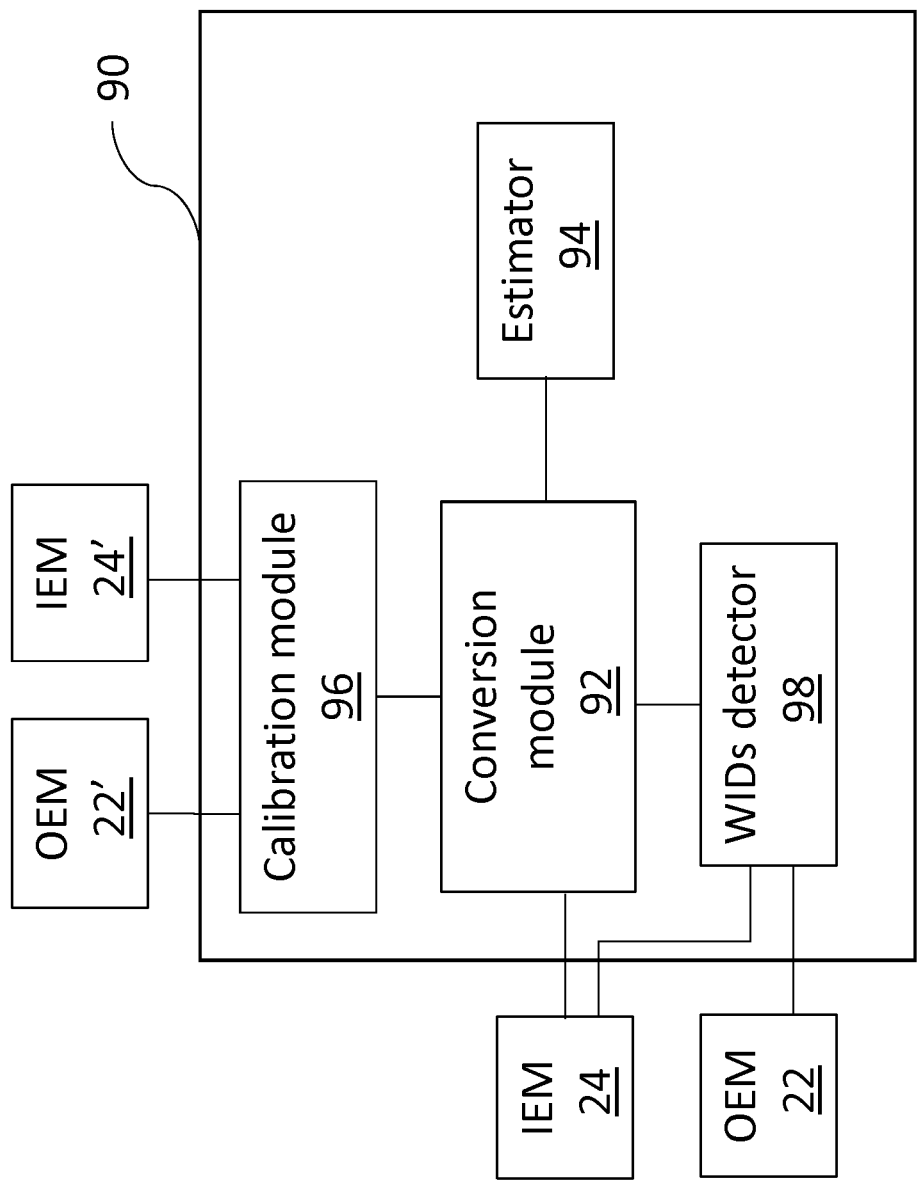
FIG. 11 presents a system for calibrating the earpieces of FIGS. 3A to 3F and adapted to detect WIDs in order to provide an effective in-ear sound pressure level measurement according to a WIDs detection, according to one embodiment.

According to one embodiment, as presented in FIG. 11, the system 90 further has a WIDs detector 98 adapted to determine if there is a WID according to measurements taken by the IEM 22 and the IEM 24. And to determine if the WID must be taken into consideration. The WID detector 98 transfers a WID indicator to the conversation module 92. The conversion module 92 converts the IEM 24 sound pressure level according to the WID indicator.

Figure 3E:
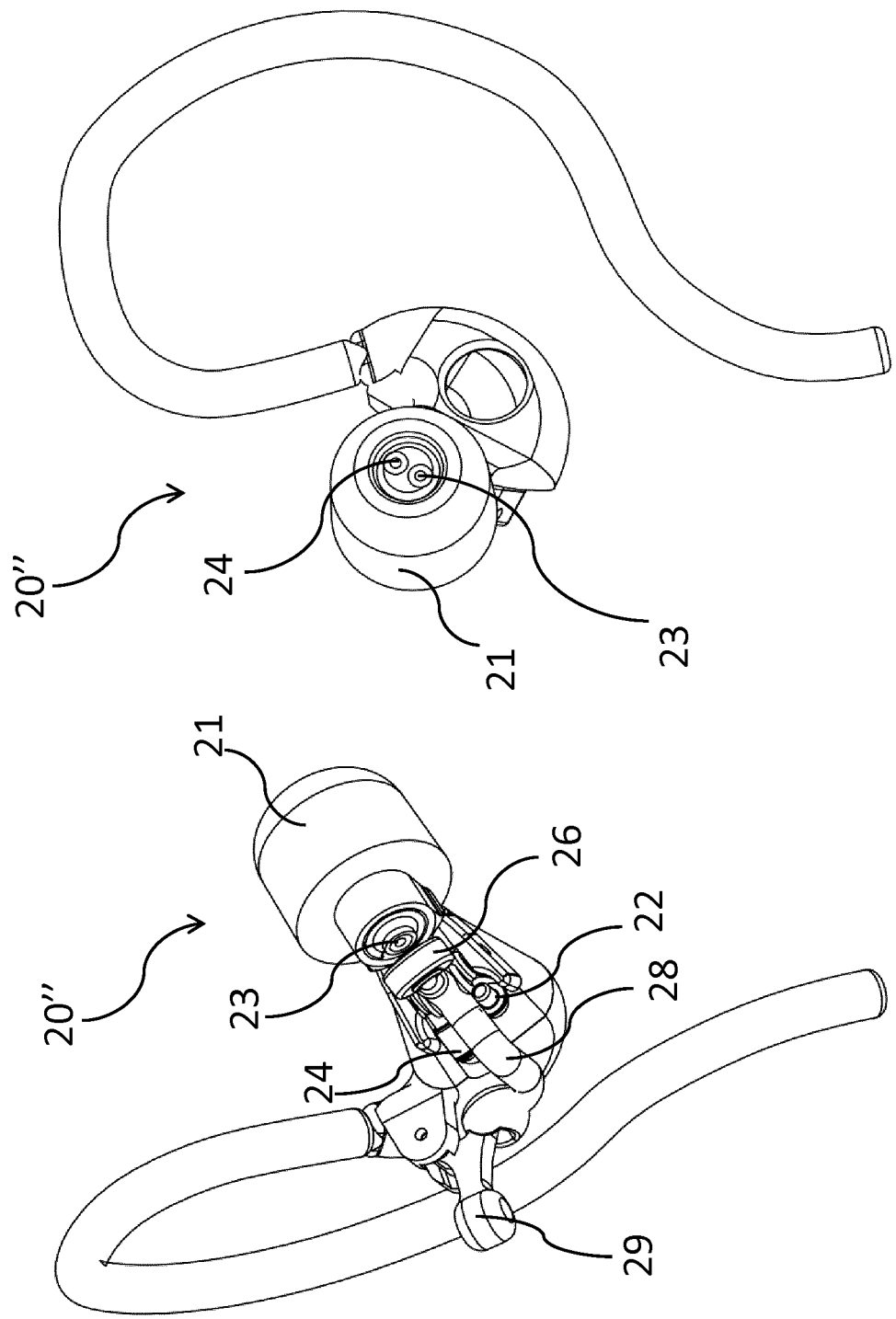
FIG. 3E presents perspective views of an occlusion earpiece having a pivotable member to actuate a removable cover over a conduit in order to allow auto-calibration of the earpiece, according to one embodiment.
Figure 3F:
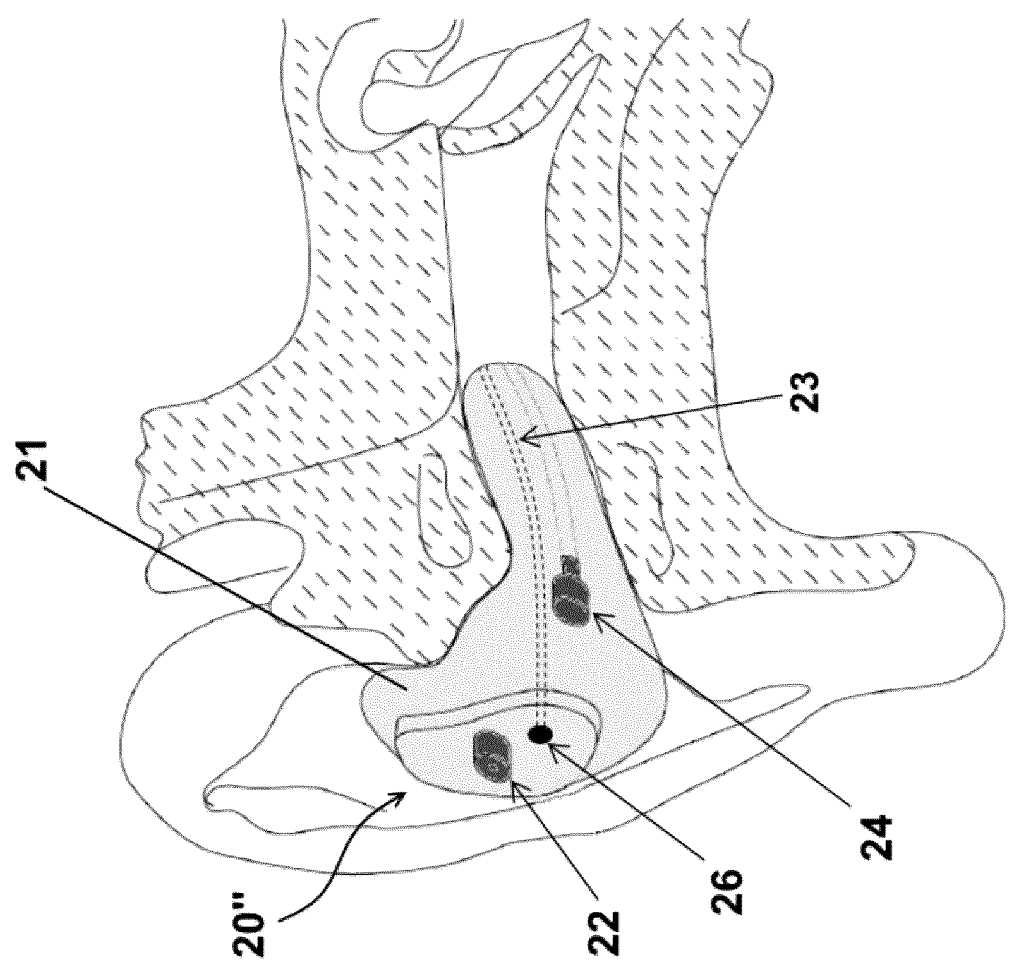
FIG. 3F presents a cross-sectional view of an occlusion earpiece, such as an earplug that is inserted into an ear-canal, the occlusion earpiece has an in-ear microphone for measuring a sound level within the ear-canal, an outer-ear microphone for measuring a sound level at an entrance of the ear-canal and a sealable opening to allow auto-calibration of the earpiece, according to one embodiment.

It shall be recognized that the earpieces 20 and 20' of FIGS. 3A to 3C and auto-calibrating earpieces 20" of FIGS. 3D to 3F can be configured to detect WIDs, without departing from the scope of the present solution.

While illustrative and presently preferred embodiment(s) of the invention have been described in detail hereinabove, it is to be understood that the inventive concepts may be otherwise variously embodied and employed and that the appended claims are intended to be construed to include such variations except insofar as limited by the prior art.

The invention claimed is:

1. A method for estimating an effective in-ear sound pressure level of an ear canal for an individual, the method comprises:
   capturing a baseline outer-ear sound pressure level outside the ear canal;
   capturing a baseline in-ear sound pressure level at an intermediate position of the ear canal;
   determining a correction factor by identifying a predetermined filter and a standing-wave minimum frequency according to a difference between the captured baseline in-ear sound pressure level and the captured baseline outer-ear sound pressure level, while the ear canal is unoccluded;
   after determining the correction factor, capturing a first sound pressure level at the intermediate position of the ear canal; and
   converting the captured first sound pressure level in an equivalent tympanic sound pressure level according to the determined correction factor.

2. The method for estimating an effective in-ear sound pressure level of claim 1, wherein the first sound pressure level is captured behind a hearing protection device.

3. The method for estimating an effective in-ear sound pressure level of claim 1, wherein estimating the effective in-ear sound pressure level is converting the measured first sound pressure level in an equivalent free field sound pressure level.

4. The method for estimating an effective in-ear sound pressure level of claim 3, wherein the correction factor is calculated by subtracting the captured baseline in-ear sound pressure level from the captured baseline outer-ear sound pressure level.

5. A method for estimating an effective in-ear sound pressure level of an ear canal for an individual, the method comprises:

capturing a baseline outer-ear sound pressure level outside the ear canal;

capturing a baseline in-ear sound pressure level at an intermediate position of the ear canal;

determining a correction factor by identifying a predetermined filter and a standing-wave minimum frequency according to a difference between the captured baseline in-ear sound pressure level and the captured baseline outer-ear sound pressure level, while the ear canal is unoccluded;

after determining the correction factor, capturing a first sound pressure level at the intermediate position of the ear canal;

converting the captured first sound pressure level in an equivalent tympanic sound pressure level according to the determined correction factor; and capturing a second sound pressure level from outside the ear canal simultaneously with the capturing of the first sound pressure level, wherein the effective in-ear sound pressure level is further estimated according to the captured second sound pressure level.

6. The method for estimating an effective in-ear sound pressure level of claim 5, wherein the estimating of the effective in-ear sound pressure level further comprises calculating an average ratio between two transfer functions associated to the captured first and the second sound pressure levels.

7. The method for estimating an effective in-ear sound pressure level of claim 6, the average ratio between two transfer functions is determined for frequencies between a predetermined minimum frequency and a predetermined maximum frequency.

8. The method for estimating an effective in-ear sound pressure level of claim 7, wherein the average ratio between two transfer functions associated to the captured first and second sound pressure levels is defined as:

$$\Delta_i = -10\log_{10}\left(\frac{\sum_{f_p=f_{min}}^{f_p=f_{max}} \gamma_i^2(f_p)}{N}\right). \quad (2)$$

9. The method for estimating an effective in-ear sound pressure level of claim 5, the method further comprising detecting wearer induced disturbance, wherein the effective in-ear sound pressure level is further estimated according to the detected wearer induced disturbance.

10. The method for estimating an effective in-ear sound pressure level of claim 9, wherein the effective in-ear noise level is further estimated according to a noise level of the detected wearer induced disturbance, for frequencies between a predetermined minimum frequency and a predetermined maximum frequency.

11. The method for estimating an effective in-ear sound pressure level of claim 10, wherein the noise level of the detected wearer induced disturbance is determined by comparing the captured first sound pressure level to a noise level threshold value.

12. The method for estimating an effective in-ear sound pressure level of claim 11, wherein the effective in-ear sound pressure level is estimated according to the captured second sound pressure level when a wearer induced disturbance is detected and when the noise level of the captured first sound pressure level is lower than the noise level threshold.

13. The method for estimating an effective in-ear sound pressure level of claim 9, wherein the wearer induced disturbance is detected according to a coherence function between the captured first sound pressure level and the captured second sound pressure level.

14. The method for estimating an effective in-ear sound pressure level of claim 13, wherein the wearer induced disturbance is detected according to an average of the coherence function over a predetermined frequency range.

15. The method for estimating an effective in-ear sound pressure level of claim 9, wherein the effective in-ear sound pressure level is estimated by ignoring the detected wearer induced disturbance.

16. The method for estimating an effective in-ear sound pressure level of claim 15, wherein the effective in-ear sound pressure level is estimated according to the captured second sound pressure level and an estimated noise reduction.

17. The method for estimating an effective in-ear sound pressure level of claim 16, wherein the estimated noise reduction is determined according to the captured first sound pressure level and the captured second sound pressure level performed when the average of the coherence function was lower than the threshold value.

18. The method for estimating an effective in-ear sound pressure level of claim 15, wherein the effective in-ear sound pressure level is estimated according to the captured first sound pressure level performed when the average of the coherence function was lower than the threshold value.

* * * * *